US011353457B2

(12) United States Patent
Shah et al.

(10) Patent No.: US 11,353,457 B2
(45) Date of Patent: Jun. 7, 2022

(54) SPECIES SPECIFIC ANTIGEN SEQUENCES FOR TICK-BORNE RELAPSING FEVER (TBRF) AND METHODS OF USE

(71) Applicant: ID-Fish Technology, Inc., Milipitas, CA (US)

(72) Inventors: Jyotsna S. Shah, Santa Clara, CA (US); Song Liu, San Jose, CA (US)

(73) Assignee: ID-Fish Technology, Inc., Milipitas (CA)

( * ) Notice: Subject to any disclaimer, the term of this patent is extended or adjusted under 35 U.S.C. 154(b) by 94 days.

(21) Appl. No.: 16/916,273

(22) Filed: Jun. 30, 2020

(65) Prior Publication Data

US 2020/0348301 A1 Nov. 5, 2020

Related U.S. Application Data

(62) Division of application No. 15/916,717, filed on Mar. 9, 2018, now Pat. No. 10,718,767.

(51) Int. Cl.

| | |
|---|---|
| ***G01N 33/569*** | (2006.01) |
| ***G01N 33/58*** | (2006.01) |
| ***G01N 33/68*** | (2006.01) |
| ***G01N 33/60*** | (2006.01) |

(52) U.S. Cl.

CPC ..... *G01N 33/56911* (2013.01); *G01N 33/581* (2013.01); *G01N 33/582* (2013.01); *G01N 33/60* (2013.01); *G01N 33/6857* (2013.01); *G01N 2333/20* (2013.01); *G01N 2469/20* (2013.01)

(58) Field of Classification Search

CPC .. G01N 33/60; G01N 2333/20; G01N 33/581; G01N 33/582; G01N 2469/20; C07K 14/20

See application file for complete search history.

(56) References Cited

U.S. PATENT DOCUMENTS

2013/0210651 A1 * 8/2013 Barbour .................. A61P 37/04 506/9

FOREIGN PATENT DOCUMENTS

WO 2011163258 A2 12/2011
WO 2016057562 A1 4/2016

OTHER PUBLICATIONS

Picken, (J Clin Microbil. Jan. 1992;30(1):99-114). (Year: 1992).*
Takano et al., (Environ Microbiol Rep Oct. 2011;3(5):632-7). (Year: 2011).*
UniProtKB/TrEMBL D5I3L2_BORHE. Immunogenic Protein A (Jun. 24, 2015) [Retrived from the Internet Apr. 24, 2019; <http://www.uniprot.org/uniprot/D5I3L2.txt?version+4>] in entirety; amino acids 25-283, 99.7% identity to SEQ ID No. 1.
Esteve-Gasent, et al. "Serological detection of tick-borne relapsing fever in Texan domestic dogs" PLOS One; Dec. 12, 2017; pp. 1-16.
Lopez, et al. "A Novel Surface Antigen of Relapsing Fever Spirochetes Can Discriminate between Relapsing Fever and Lyme Borreliosis" Clinical and Vaccine Immunology; 2010; vol. 17; No. 4; pp. 564-571.

(Continued)

*Primary Examiner* — Jana A Hines
(74) *Attorney, Agent, or Firm* — Pierce Atwood LLP; Kevin M. Farrell

(57) ABSTRACT

Compositions and methods for the detection and identification of Tick-Borne Relapsing Fever *Borrelia* sp. antibodies.

9 Claims, 1 Drawing Sheet

Specification includes a Sequence Listing.

Tick-Borne Relapsing Fever Borrelia Immunoblot

(56) References Cited

OTHER PUBLICATIONS

Lopez, et al. “Sequence Analysis and Serological Responses against Borrelia turicatae BipA, a Putative Species-Specific Antigen” Neglected Tropical Diseases; 2013; vol. 17; Issue 9; 8 pages.
Tokarz, et al. “A multiplex serologic platform for diagnosis of tick-borne diseases” Scientific Reports; 2018; 10 pages.
Sudhindra, et al. “Insights into Borrelia miyamotoi infection from an untreated case demonstrating relapsing fever, monocytosis and a positive C6 Lyme serology” Diagnostic Microbiology and Infectious Disease; 2016; pp. 93-96.
Porcella, et al. “Serodiagnosis of Louse-Borne Relapsing Fever with Glycerophosphodiester Phosphodiesterase (GlpQ) from Borrelia recurrentis” Journal of Microbiology; 2000; vol. 38; No. 10; pp. 3561-3571.

* cited by examiner

Tick-Borne Relapsing Fever Borrelia Immunoblot
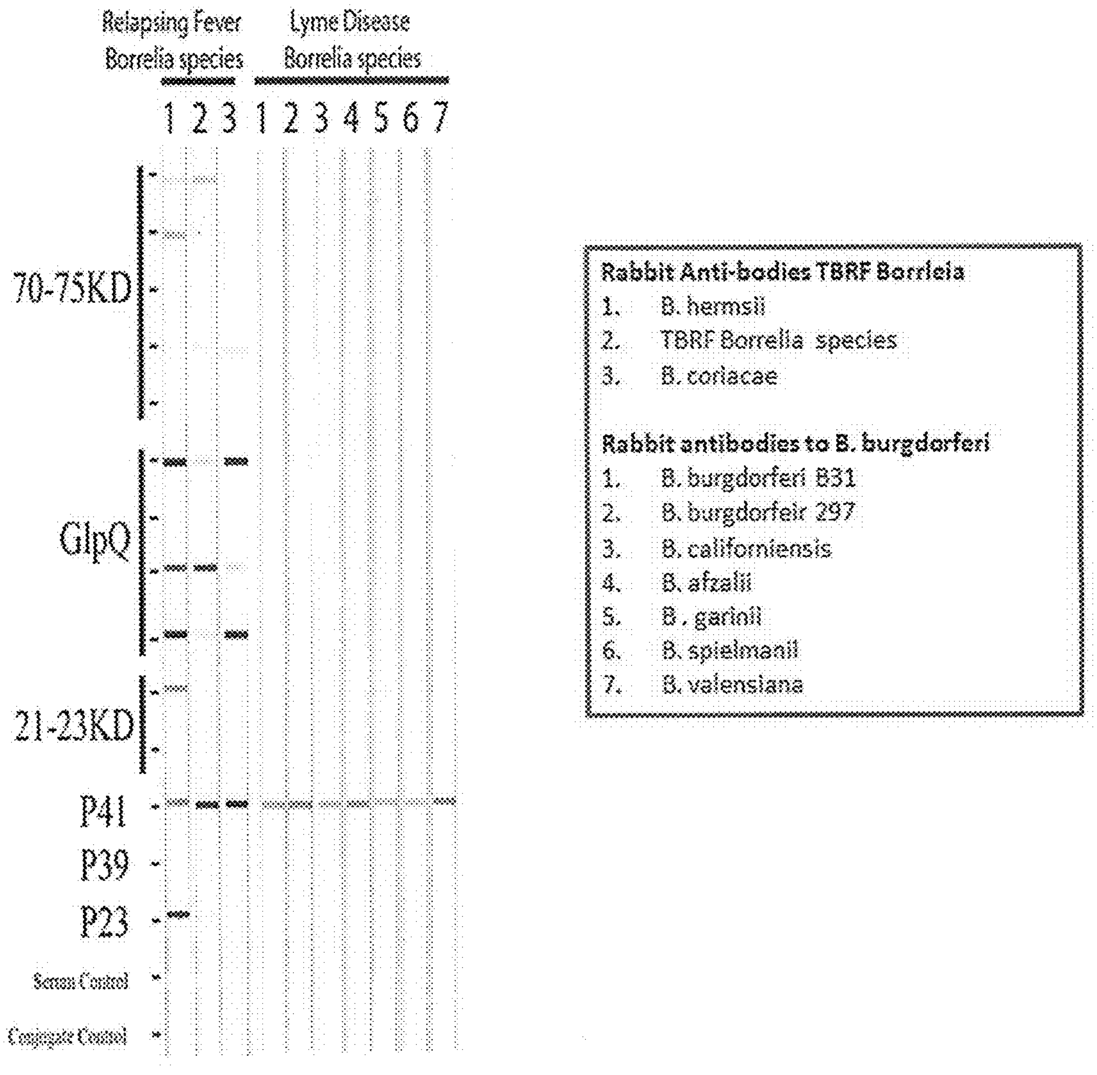

SEQUENCE LISTING

<160> NUMBER OF SEQ ID NOS: 20

<210> SEQ ID NO 1
<211> LENGTH: 259
<212> TYPE: PRT
<213> ORGANISM: Borrelia hermsii

<400> SEQUENCE: 1

Met Ser Glu Ser Asn Trp Glu Ile Asp Glu Pro Gly Ser Val Gln Asp
1 5 10 15

-continued

```
Ile Arg Asn Ser Val Ala Ser Glu Leu Gln Lys Pro Glu Asn Ile Gly
            20                  25                  30

Gln Arg Gly Lys Ser Val Gly Lys Glu Val Gly Lys Asp Ala Ala Ala
        35                  40                  45

Ser Gly Glu Gly Ala Val Val Ala Val Gly Ser Lys Gln Asn Thr Leu
    50                  55                  60

Gln Asn Ser Glu Asn Ser Ser Gln Glu Gly Ala Gly Ser Ala Leu Gln
65                  70                  75                  80

Lys Pro Gly Asp Ser Pro Gln Lys Gly Val Ala Ser Gln Glu Gly Thr
                85                  90                  95

Asn Gly Ala Leu Gln Gly Val Val Ala Ala Gly Gly Val Ser Val Gly
            100                 105                 110

Gly Ser Gly Val Gly Ala Ala Ala Ser Asp Gly Asn Ser Ser Ser Ser
        115                 120                 125

Gln Glu Ala Glu Ser Val Asp Leu Lys Asn Val Leu Ala Asp Ser His
    130                 135                 140

Gly Val Gly Ala Ser Asn Leu Asn Ile Lys Ala Glu Gly Asp Ile Ser
145                 150                 155                 160

Thr Gly His Gly Thr Glu Gly Val Ile Ala Ser Gly Asp Leu Thr Asn
                165                 170                 175

Thr Ile Ile Thr Ser Gly Val Thr Ala Ala Ala Ser Pro Ala Ile Val
            180                 185                 190

Ser Gly Asp Glu Arg Gly Val Ala Ala Ile Lys Asp Ser Ile Ala Val
        195                 200                 205

Val Leu Glu Thr Gln Lys Glu Ala Gln Lys Glu Thr Glu Lys Glu Thr
    210                 215                 220

Glu Asn Val Lys Phe Ala Val Leu Gly Thr Val Lys Lys Ile Val Asp
225                 230                 235                 240

Gly Val Ala Asp Gly Ile Ala Asn Val Ile Glu Tyr Gly Leu Glu Asn
                245                 250                 255

Gly Ile Asp


<210> SEQ ID NO 2
<211> LENGTH: 257
<212> TYPE: PRT
<213> ORGANISM: Borrelia hermsii

<400> SEQUENCE: 2

Met Asn Lys Val Lys Asp Gly Ile Lys Thr Ala Ser Lys Gly Ala Glu
1               5                   10                  15

Thr Phe Val Thr Ala Ala Met Gln Gly Ala Gly Ala Val Leu Gly Ser
            20                  25                  30

Leu Gln Asp Val Gly Asn Phe Val Met Asp Ala Thr Leu Ser Met Gly
        35                  40                  45

Asp Met Phe Ala Gly Ile Lys Ser Asp Ser Asp Val Ser Ser Ala Asn
    50                  55                  60

Ser Gly Met Thr Val Asn Ser Gly Met Thr Val Ser Leu Ser Ser Asn
65                  70                  75                  80

Glu Thr Gln Val Ile Gly His Leu Glu Glu Tyr Leu Lys Ser Ala Ile
                85                  90                  95

Lys Val Asn Gly Asn Glu Ser Ser Arg Gln Ser Lys Leu Glu Asn Gly
            100                 105                 110

Arg Gln Lys Phe Phe Ala Trp Leu Arg Glu Lys Asp Thr Asp Phe Ser
        115                 120                 125
```

-continued

```
Lys Arg Lys Glu Leu Val Gln Ala Met Gln Arg Val Tyr Asn Phe Ile
    130                 135                 140

Lys Glu Lys Ser Ser Asn Ser Arg Glu Leu Gln Thr Trp Val Leu Gly
145                 150                 155                 160

Val Val Gly Asp Asp Asp Thr Val Val Asp Val Asp Arg Asp Asp Glu
                165                 170                 175

Leu Asn Ser Asp Val Glu Ile Asp Phe Leu Ile Lys Lys Thr Leu Ser
            180                 185                 190

Ser Arg Asp Tyr Ser Gly Phe Ala Val Ser Leu Leu Phe Gln Ala Leu
        195                 200                 205

Ala Asp Thr Leu Tyr Asp Ala Glu Asn Asp Arg Asp Lys Pro Glu Glu
    210                 215                 220

Gln Ile Phe Lys Asp Leu Lys Ala Val Phe Ser Asp Asn Ala Gly Glu
225                 230                 235                 240

Asp Lys Gly Phe Gly Glu Phe Lys Ser Ile Ile Glu Asp Lys Ser Gln
                245                 250                 255

Ala


<210> SEQ ID NO 3
<211> LENGTH: 260
<212> TYPE: PRT
<213> ORGANISM: Borrelia miyamotoi

<400> SEQUENCE: 3

Met Ala Lys Ala Gly Asn Phe Asp Glu Val Leu Asp Leu Asp Gly Asp
1               5                   10                  15

Asp Glu Glu Ala Glu Ile Asp Glu Ile Glu Gln Asn Leu Ser Glu Gly
            20                  25                  30

Val Asp Gly Asn Ile Asp Gln Asn Pro Gly Asn Val Asp Gly His Ile
        35                  40                  45

Val Leu Val Asp Ala Gln Gly Val Ser Val Pro Thr Val Val Glu His
    50                  55                  60

Ser Ala Val Ser Ser Ser Val Glu Arg Arg Val Val Thr Val Gly Gln
65                  70                  75                  80

Asn Val Glu Ser Arg Arg Leu Thr Lys Val Glu Arg Leu Glu Lys Tyr
                85                  90                  95

Leu Glu Ser Ala Ile Lys Ser Gly Gly Lys Leu Asn Glu Gln Gln Arg
            100                 105                 110

Arg Leu Lys Asn Gly Lys Gln Met Leu Phe Thr Trp Leu Asn Glu Asp
        115                 120                 125

Ala Asn Ala Ser Lys Arg Ala Glu Leu Glu Gln Asp Met Gln Lys Leu
    130                 135                 140

Tyr Gly Leu Ile Lys Glu Ser Ile Thr Asp Ser Ser Ser Gln Phe Ser
145                 150                 155                 160

Ser Arg Asp Gly Glu Tyr Ser Asp Glu Ala Ile Asp Gly Leu Leu Asn
                165                 170                 175

Ser Leu Phe Ser Ser Ser Phe Asp Asn Thr Phe Ala Leu Asp Leu Phe
            180                 185                 190

Phe Gln Ala Leu Leu Asn Thr Leu Cys Asp Phe Lys Lys Asp Asn Cys
        195                 200                 205

Lys Asp Glu Glu Val Ile Phe Ala Asp Ile Arg Lys Val Phe Ser Asp
    210                 215                 220

Glu Ser Asp Thr Lys Gly His Phe Gly Tyr Leu Lys Ser Lys Leu Lys
225                 230                 235                 240
```

-continued

Asp Glu Leu Val Ile Ser Asp Glu Gly Asp Tyr Gly Glu Asp Glu Asp
245 250 255

Phe Glu Glu Asp
260

<210> SEQ ID NO 4
<211> LENGTH: 224
<212> TYPE: PRT
<213> ORGANISM: Borrelia turcica

<400> SEQUENCE: 4

Met Glu Glu Glu Ala Ser Ile Glu Ser Glu Ala Met Pro Leu Asp Glu
1 5 10 15

Ala Lys Ile Ser Ser Leu Asp Lys Glu Thr Val Pro Ala Val Gln Ala
20 25 30

Asp Gly Thr Pro Glu Gln Ile Val Ala Ser Val Gly Leu Glu Gly Glu
35 40 45

Glu Ser Lys Lys Phe Glu His Leu Lys Gly Ser Leu Gly Asp Ala Ile
50 55 60

Lys Val Asn Gly Lys Gly Glu Glu Lys Arg Lys Glu Asn Glu Glu Arg
65 70 75 80

Gln Lys Glu Phe Phe Asp Trp Leu Asp Lys Asn Asp Pro Asp Leu Ser
85 90 95

Lys Arg Lys Glu Leu Ala Glu Leu Met Lys Lys Val Tyr Gly Leu Leu
100 105 110

Lys Glu His Ala Gln Asn Ser Glu Gln Ile Lys Ser Phe Val Glu Gly
115 120 125

Thr Pro Lys Asp Glu Asn Val Lys Lys Ile Gly Val Thr Ser Ala Arg
130 135 140

Asp Ile Lys Thr Asp Glu Gln Val Glu Ala Leu Ile Lys Ala Val Leu
145 150 155 160

Gly His Ser Glu Glu Ser Gly Thr Asn Leu Ser Leu Phe Phe Gln Lys
165 170 175

Leu Gly Asp Ala Phe Gly Thr Glu Asp Gly Glu Ser Gln Lys Ser Asn
180 185 190

Glu Lys Ile Leu Glu Glu Leu Lys Arg Val Cys Glu Ser Ser Asp Glu
195 200 205

Ile Lys Lys Leu Lys Glu Asp Leu Lys Ile Glu Glu Lys Val Gln Ser
210 215 220

<210> SEQ ID NO 5
<211> LENGTH: 226
<212> TYPE: PRT
<213> ORGANISM: Borrelia turcica

<400> SEQUENCE: 5

Met Asn Ile Asp Ala Val Ala Asp Leu Leu Ala Asp Gln Gln Glu Ala
1 5 10 15

Ala Ser Thr Gly Leu Lys Asp Ala Ser Thr Gly Leu Lys Asp Thr Ser
20 25 30

Thr Gly Leu Ser Lys Leu Asp Lys Lys Glu Lys Lys Val Ser Ser Leu
35 40 45

Lys Glu Thr Leu Glu Asn Ser Ser Asn Val Leu Tyr Glu Ser Ser Ser
50 55 60

Pro Thr Lys Thr Arg Gln Glu Glu Phe Phe Lys Trp Leu Glu Glu Asn
65 70 75 80

-continued

```
Asp Ser Asp Tyr Ser Lys Arg Lys Gln Leu Glu Glu Ser Met Asp Lys
                85                  90                  95

Val Phe Ser Leu Ile Lys Asp Ser Ala Ser Ser Ser Thr Glu Ile Lys
            100                 105                 110

Glu Ile Ile Ala Lys Gly Gln Ser Asp Ala Gly Ile Ile Lys Ala Gly
        115                 120                 125

Ile Lys Thr Ala Asp Asp Ile Lys Thr Asp Glu Gln Val Asp Ala Leu
    130                 135                 140

Val Lys Phe Val Thr Gly Thr Gly Asp Asp Leu Asp Leu Glu Ser Gly
145                 150                 155                 160

Ser Ser Ser Ile Lys Ala Phe Phe Gly Thr Leu Ala Glu Val Phe Asp
                165                 170                 175

Asp Asp Leu Asn Asp Val Met Thr Asp Lys Lys Gly Gln Lys Arg Gly
            180                 185                 190

His Asp Lys Val Phe Glu Asp Leu Lys Lys Val Phe Ser Glu Asp Ser
        195                 200                 205

Asp Gly Pro Phe Asp Ile Leu Lys Asp Ala Leu Lys Gln Ala Leu Lys
    210                 215                 220

Asn Asn
225


<210> SEQ ID NO 6
<211> LENGTH: 250
<212> TYPE: PRT
<213> ORGANISM: Borrelia turicatae

<400> SEQUENCE: 6

Met Ser Thr Ser Tyr Trp Ser Val Asp Asn Asp Gly Phe Val Gln Gly
1               5                   10                  15

Thr Lys Ser Phe Val Asp Ser Pro Leu Arg Lys Pro Asp Arg Phe Asp
            20                  25                  30

Gln Glu Val Ser Ala Gly Gly Lys Lys Ile Glu Lys Ala Val Ser Arg
        35                  40                  45

Asn Leu Arg Val Ala Gly Gly Gln Arg Gln Gly Ile Ala Asp Asp Gly
    50                  55                  60

Ile Gly Val Ala Gly Val Arg Glu Ala Gly Gly Val Leu Lys Asp Ala
65                  70                  75                  80

Gly Asn Ala Val Gln Arg Asp Ile Asn Gly Ser Gly Glu Gly Ile Lys
                85                  90                  95

Asn Asp Val Ile Gln Asn Pro Glu Gly Val Gly Val Gln Val Ala Val
            100                 105                 110

Gly Ser Ala Asp Thr Gly Ala Asp Ser Gly Gln Glu Ala Gly Lys Val
        115                 120                 125

Phe Gln Asn Leu Gly Asp Thr Gly Thr Gln Ser Ile Gln Arg Val Val
    130                 135                 140

Ser Ser Ser Asp Leu Asn Ser Asp Leu Gly Val Gly Ser Lys Asp Gly
145                 150                 155                 160

Ile Ser Thr Asn Gly Met Ser Thr Asn His Val Thr Glu Asn Glu Asn
                165                 170                 175

Ser Ile Asn Ser Ile Thr Ser Thr Ser Ser Gly Leu Asn Thr Ala Leu
            180                 185                 190

Gln Met Ala Gly Thr Ser Thr Arg Thr Ser Gly Tyr Glu Gly Glu Ile
        195                 200                 205

Thr Thr Asn Thr Gln Asp Arg Thr Phe Val Glu Thr Gly Thr Gln Asp
    210                 215                 220
```

-continued

```
Ser Lys Ala Gln Tyr Ser Asp Phe Ser Asp Gln Asp Ile Arg Asp Lys
225                 230                 235                 240

Val Leu Gly Ser Val Val Gly Gly Val Val
                245                 250


<210> SEQ ID NO 7
<211> LENGTH: 334
<212> TYPE: PRT
<213> ORGANISM: Borrelia hermsii

<400> SEQUENCE: 7

Met Ala Ser Met Thr Gly Gly Gln Gln Met Gly Arg Gly Ser Glu Lys
1               5                   10                  15

Met Ser Gln Asn Gln Lys Ser Pro Leu Val Ile Ala His Arg Gly Ala
            20                  25                  30

Ser Gly Tyr Leu Pro Glu His Thr Leu Glu Ala Lys Ala Tyr Ala Tyr
        35                  40                  45

Ala Leu Gly Ala Asp Tyr Leu Glu Gln Asp Ile Val Leu Thr Lys Asp
    50                  55                  60

Asn Ile Pro Val Ile Met His Asp Pro Glu Leu Asp Thr Thr Thr Asn
65                  70                  75                  80

Val Ala Lys Leu Phe Pro Glu Arg Ala Arg Glu Asn Gly Arg Tyr Tyr
                85                  90                  95

Ser Val Asp Phe Thr Leu Asp Glu Leu Lys Ser Leu Ser Leu Ser Glu
            100                 105                 110

Arg Phe Asp Pro Ala Ser Arg Asn Pro Ile Tyr Pro Asn Arg Phe Pro
        115                 120                 125

Leu Asn Glu His Asp Phe Lys Ile Pro Thr Leu Glu Glu Glu Ile Gln
    130                 135                 140

Phe Ile Gln Gly Leu Asn Lys Ser Thr Gly Arg Asn Val Gly Ile Tyr
145                 150                 155                 160

Pro Glu Ile Lys Lys Pro Leu Trp His Lys Gln Gln Gly Lys Asp Ile
                165                 170                 175

Ser Lys Ile Val Ile Glu Ile Leu Asn Lys Tyr Gly Tyr Lys Ser Lys
            180                 185                 190

Glu Asp Lys Ile Tyr Leu Gln Thr Phe Asp Phe Asp Glu Leu Lys Arg
        195                 200                 205

Ile Arg Glu Glu Leu Gly Tyr Gln Gly Lys Leu Ile Met Leu Val Gly
    210                 215                 220

Glu Asn Asp Trp Asp Glu Ala Pro Thr Asp Tyr Glu Tyr Ile Lys Ser
225                 230                 235                 240

Glu Glu Gly Met Ala Glu Val Ala Lys Tyr Ser Asp Gly Ile Gly Pro
                245                 250                 255

Trp Ile Pro Gln Ile Ile Ile Glu Gly Lys Ile Thr Asp Leu Thr Ser
            260                 265                 270

Leu Ala His Lys His Asn Met Glu Val His Pro Tyr Thr Phe Arg Ile
        275                 280                 285

Asp Ala Leu Pro Ser Tyr Val Lys Asp Ala Asp Glu Leu Leu Asp Leu
    290                 295                 300

Leu Phe Asn Lys Ala Lys Val Asp Gly Ile Phe Thr Asp Phe Thr Asp
305                 310                 315                 320

Thr Val Val Asn Phe Ile Thr Lys Ile Lys Pro Lys Gly Glu
                325                 330
```

-continued

<210> SEQ ID NO 8
<211> LENGTH: 254
<212> TYPE: PRT
<213> ORGANISM: Borrelia miyamotoi

<400> SEQUENCE: 8

```
Met Ala Ser Met Thr Gly Gly Gln Gln Met Gly Arg Gly Ser Glu Met
1               5                   10                  15

Gly Glu Asn Lys Lys Ser Pro Leu Ile Ile Ala His Arg Gly Ala Ser
            20                  25                  30

Gly Tyr Leu Pro Glu His Thr Leu Glu Ala Lys Ala Tyr Ala Tyr Ala
        35                  40                  45

Leu Gly Ala Asp Tyr Leu Glu Gln Asp Ile Val Leu Thr Lys Asp Asn
    50                  55                  60

Ile Pro Val Ile Met His Asp Pro Glu Ile Asp Thr Thr Thr Asn Val
65                  70                  75                  80

Ala Gln Leu Phe Pro Asn Arg Ala Arg Glu Asn Gly Arg Tyr Tyr Ala
                85                  90                  95

Thr Asp Phe Thr Leu Thr Glu Leu Lys Ser Leu Asn Leu Ser Glu Arg
            100                 105                 110

Phe Asp Pro Glu Asn Lys Lys Pro Ile Tyr Pro Asn Arg Phe Pro Leu
        115                 120                 125

Asn Glu Tyr Asn Phe Lys Ile Pro Thr Leu Glu Glu Glu Ile Gln Phe
    130                 135                 140

Ile Gln Gly Leu Asn Lys Ser Thr Gly Lys Asn Val Gly Ile Tyr Pro
145                 150                 155                 160

Glu Ile Lys Lys Pro Phe Trp His Lys Gln Gln Gly Lys Asp Ile Ser
                165                 170                 175

Lys Ile Val Ile Glu Ile Leu Asn Lys Tyr Gly Tyr Lys Ser Lys Glu
            180                 185                 190

Asp Lys Ile Tyr Leu Gln Thr Phe Asp Phe Asp Glu Leu Lys Arg Ile
        195                 200                 205

Arg Lys Glu Leu Gly Tyr Gln Gly Lys Leu Ile Met Leu Val Gly Glu
    210                 215                 220

Asn Asp Trp Asn Glu Ala Pro Thr Asp Tyr Glu Tyr Ile Lys Ser Glu
225                 230                 235                 240

Glu Gly Ile Ala Glu Val Ala Lys Tyr Ser Asp Gly Ile Gly
                245                 250
```

<210> SEQ ID NO 9
<211> LENGTH: 327
<212> TYPE: PRT
<213> ORGANISM: Borrelia turcica

<400> SEQUENCE: 9

```
Met Ala Ser Met Thr Gly Gly Gln Gln Met Gly Arg Gly Ser Lys Val
1               5                   10                  15

Ser Met Asn Lys Ala Leu Pro Leu Val Ile Ala His Arg Gly Ala Ser
            20                  25                  30

Gly Tyr Leu Pro Glu His Thr Leu Glu Ala Lys Ala Phe Ala Tyr Ala
        35                  40                  45

Leu Gly Ala His Tyr Leu Glu Gln Asp Ile Val Leu Thr Lys Asp Asp
    50                  55                  60

Ile Pro Ile Ile Met His Asp Pro Glu Ile Asp Thr Thr Thr Asn Val
65                  70                  75                  80

Ala Glu Ile Phe Pro Glu Arg Ala Arg Lys Asp Gly Arg Tyr Tyr Ser
```

-continued

```
                85                  90                  95

Val Asp Phe Thr Leu Arg Glu Leu Lys Ser Leu Lys Leu Ser Glu Arg
            100                 105                 110

Phe Asp Pro Lys Thr Gly Lys Pro Ile Tyr Pro Asn Arg Phe Pro Leu
        115                 120                 125

Asn Glu Tyr Asn Phe Lys Ile Pro Thr Leu Glu Glu Glu Ile Gln Phe
    130                 135                 140

Ile Gln Gly Leu Asn Lys Ser Thr Gly Arg Asn Val Gly Ile Tyr Pro
145                 150                 155                 160

Glu Ile Lys Lys Pro Phe Trp His Lys Gln Gln Gly Lys Asp Ile Ser
                165                 170                 175

Lys Ile Val Ile Glu Met Leu Asn Lys Tyr Gly Tyr Lys Ser Lys Glu
            180                 185                 190

Asp Lys Ile Tyr Leu Gln Ile Phe Asp Phe Asp Glu Leu Lys Arg Ile
        195                 200                 205

Arg Glu Glu Leu Gly Tyr Lys Gly Lys Leu Val Met Leu Ile Gly Glu
    210                 215                 220

Asn Asp Trp Asn Glu Ala Pro Thr Asp Tyr Glu Tyr Ile Lys Ser Glu
225                 230                 235                 240

Glu Gly Ile Ala Glu Val Ala Lys Tyr Ser Asp Gly Ile Gly Pro Trp
                245                 250                 255

Ile Pro Gln Val Ile Ile Asp Gly Lys Val Thr Gly Leu Thr Ser Leu
            260                 265                 270

Ala His Lys His Lys Met Glu Val His Pro Tyr Thr Met Arg Ile Asp
        275                 280                 285

Ala Leu Pro Ser Tyr Val Lys Asp Ala Asn Glu Leu Leu Asn Leu Leu
    290                 295                 300

Phe Asn Lys Ala Lys Val Asp Gly Val Phe Thr Asp Phe Pro Asp Val
305                 310                 315                 320

Val Leu Gly Phe Ile Arg Lys
                325


<210> SEQ ID NO 10
<211> LENGTH: 329
<212> TYPE: PRT
<213> ORGANISM: Borrelia turicatae

<400> SEQUENCE: 10

Met Ala Ser Met Thr Gly Gly Gln Gln Met Gly Arg Gly Ser Glu Lys
1               5                   10                  15

Met Ser Met Thr Asn Lys Lys Pro Pro Leu Ile Ile Ala His Arg Gly
            20                  25                  30

Ala Ser Gly Tyr Leu Pro Glu His Thr Leu Glu Ala Lys Ala Phe Ala
        35                  40                  45

Tyr Ala Leu Gly Ala Asp Tyr Leu Glu Gln Asp Ile Val Leu Thr Lys
    50                  55                  60

Asp Asn Val Pro Ile Ile Met His Asp Pro Glu Leu Asp Thr Thr Thr
65                  70                  75                  80

Asn Val Ala Lys Leu Phe Pro Glu Arg Ala Arg Glu Asn Gly Arg Tyr
                85                  90                  95

Tyr Ser Val Asp Phe Thr Leu Asp Glu Leu Lys Ser Leu Ser Leu Ser
            100                 105                 110

Glu Arg Phe Asp Leu Glu Thr Arg Lys Pro Ile Tyr Pro Asn Arg Phe
        115                 120                 125
```

-continued

```
Pro Leu Asn Glu Tyr Asn Val Lys Ile Pro Thr Leu Glu Glu Glu Ile
    130                 135                 140

Gln Phe Ile Gln Gly Leu Asn Lys Ser Thr Gly Arg Asn Val Gly Ile
145                 150                 155                 160

Tyr Pro Glu Ile Lys Lys Pro Leu Trp His Lys Gln Gln Gly Lys Asp
                165                 170                 175

Ile Ser Lys Ile Val Ile Glu Ile Leu Asn Lys Tyr Gly Tyr Lys Ser
            180                 185                 190

Lys Glu Asp Lys Ile Tyr Leu Gln Thr Phe Asp Phe Asp Glu Leu Lys
        195                 200                 205

Arg Ile Arg Glu Glu Leu Gly Tyr Gln Gly Lys Leu Ile Met Leu Val
    210                 215                 220

Gly Glu Asn Asp Trp Asp Glu Ala Pro Thr Asp Tyr Glu Tyr Ile Lys
225                 230                 235                 240

Ser Gln Glu Gly Met Thr Glu Val Ala Lys Tyr Ala Asp Gly Ile Gly
                245                 250                 255

Pro Trp Ile Pro Gln Ile Ile Ile Asp Gly Lys Ile Thr Asp Leu Thr
            260                 265                 270

Ser Leu Ala His Lys Tyr Asn Met Glu Val His Ala Tyr Thr Phe Arg
        275                 280                 285

Ile Asp Ser Leu Pro Ser Tyr Val Lys Asp Ala Asn Glu Leu Leu Asp
    290                 295                 300

Leu Leu Phe Asn Lys Ala Lys Ile Asp Gly Leu Phe Thr Asp Phe Thr
305                 310                 315                 320

Asp Thr Val Val Lys Phe Val Lys Gln
                325


<210> SEQ ID NO 11
<211> LENGTH: 171
<212> TYPE: PRT
<213> ORGANISM: Borrelia hermsii

<400> SEQUENCE: 11

Met Ala Ser Met Thr Gly Gly Gln Gln Met Gly Arg Gly Ser Ser Asp
1               5                   10                  15

Ala Asn Leu Leu Lys Thr Leu Asp Asn Asn Gln Lys Gln Ala Leu Ile
            20                  25                  30

Tyr Phe Lys Asp Thr Leu Gln Asp Lys Lys Tyr Leu Asn Asp Leu Thr
        35                  40                  45

Ala Ser Gln Lys Asn Phe Leu Asp Asp Leu Glu Lys Asn Lys Lys Asp
    50                  55                  60

Pro Gly Leu Gln Asp Lys Leu Lys Lys Thr Leu Ser Ser Glu Tyr Asp
65                  70                  75                  80

Gly Ser Gln Phe Asn Lys Leu Leu Asn Glu Leu Gly Asn Ala Lys Val
                85                  90                  95

Lys Gln Phe Leu Gln Gln Leu His Ile Met Leu Gln Ser Ile Lys Asp
            100                 105                 110

Gly Thr Leu Thr Ser Phe Ser Tyr Ala Asn Phe Lys Asp Leu Gln Thr
        115                 120                 125

Leu Glu Gln Lys Lys Glu Arg Ala Leu Gln Tyr Ile Asn Gly Arg Leu
    130                 135                 140

Tyr Val Glu Tyr Tyr Phe Tyr Ile Asn Gly Ile Ser Asn Ala Asp Asn
145                 150                 155                 160

Phe Phe Glu Ser Val Met Gln Leu Leu Glu Thr
                165                 170
```

<210> SEQ ID NO 12
<211> LENGTH: 169
<212> TYPE: PRT
<213> ORGANISM: Borrelia miyamotoi

<400> SEQUENCE: 12

```
Met Leu Asp His Asn Leu Gln Pro Asn Lys Ile Asn Asn Ile Ile Ser
1               5                   10                  15

Ser Leu Asp Ser Asn Gln Lys Gln Ala Leu Ile Phe Phe Lys Asn Leu
            20                  25                  30

Val Lys Asn Lys Gln Tyr Ser Lys Asp Leu Glu Gln Ala Ser Lys Ser
        35                  40                  45

Tyr Leu Glu Asn Leu Lys Glu Lys Asn Asn Gln Asn Leu Asn Leu Gln
    50                  55                  60

Asn Lys Leu Asn Gln Gly Leu Asn Cys Asp Tyr Asp Asp Ser Lys Ile
65                  70                  75                  80

Glu Lys Leu Phe Asp Gln Leu Gly Asn Asp Lys Met Lys Lys Phe Leu
                85                  90                  95

Gln Gln Leu His Leu Met Leu Lys Ser Ile Asn Asp Gly Thr Leu Ile
            100                 105                 110

Ser Phe Ser Ser Ser Asn Phe Arg Asp Thr Thr Thr Leu Ser Gln Lys
        115                 120                 125

Lys Glu Lys Ala Leu Glu Tyr Ile Lys Ser Gln Leu Tyr Ile Glu Phe
    130                 135                 140

Tyr Phe His Ser Asn Asp Ile Ser Asp Thr Glu Phe Phe Phe Gln Arg
145                 150                 155                 160

Thr Ile Ala Leu Leu Glu Thr Gln Asn
                165
```

<210> SEQ ID NO 13
<211> LENGTH: 322
<212> TYPE: PRT
<213> ORGANISM: Borrelia hermsii

<400> SEQUENCE: 13

```
Met Arg Asn Asn Ser Ile Asn Ala Thr Asn Leu Ser Lys Thr Gln Glu
1               5                   10                  15

Lys Leu Ser Ser Gly His Arg Ile Asn Arg Ala Ser Asp Asp Ala Ala
            20                  25                  30

Gly Met Gly Val Ala Gly Lys Ile Asn Ala Gln Ile Arg Gly Leu Ser
        35                  40                  45

Gln Ala Ser Arg Asn Thr Ser Lys Ala Ile Asn Phe Ile Gln Thr Thr
    50                  55                  60

Glu Gly Asn Leu Asn Glu Val Glu Arg Val Leu Val Arg Met Lys Glu
65                  70                  75                  80

Leu Ala Val Gln Ser Gly Asn Gly Thr Tyr Ser Asp Ala Asp Arg Gly
                85                  90                  95

Ser Ile Gln Ile Glu Ile Glu Gln Leu Thr Asp Glu Ile Asn Arg Ile
            100                 105                 110

Ala Asp Gln Ala Gln Tyr Asn Gln Met His Met Leu Ser Asn Lys Ser
        115                 120                 125

Ala Ala Gln Asn Val Lys Thr Ala Glu Glu Leu Gly Met Gln Pro Ala
    130                 135                 140

Lys Ile Asn Thr Pro Ala Ser Leu Ala Gly Ser Gln Ala Ser Trp Thr
145                 150                 155                 160
```

-continued

```
Leu Arg Val His Val Gly Ala Asn Gln Asp Glu Ala Ile Ala Val Asn
                165                 170                 175

Ile Tyr Ala Ser Asn Val Ala Asn Leu Phe Ala Gly Glu Gly Ala Gln
            180                 185                 190

Ala Ala Pro Val Gln Glu Ile Gly Gln Gln Glu Glu Gly Gln Ala Ala
        195                 200                 205

Pro Ala Pro Ala Ala Ala Pro Ala Gln Gly Gly Val Asn Ser Pro Ile
    210                 215                 220

Asn Val Thr Thr Ala Val Asp Ala Asn Met Ser Leu Ala Lys Ile Glu
225                 230                 235                 240

Gly Ala Ile Arg Met Val Ser Asp Gln Arg Ala Asn Leu Gly Ala Phe
                245                 250                 255

Gln Asn Arg Leu Glu Ser Ile Lys Asp Ser Thr Glu Tyr Ala Ile Glu
            260                 265                 270

Asn Leu Lys Ala Ser Tyr Ala Gln Ile Lys Asp Ala Thr Met Thr Asp
        275                 280                 285

Glu Val Val Ala Ser Thr Thr His Ser Ile Leu Thr Gln Ser Ala Met
    290                 295                 300

Ala Met Ile Ala Gln Ala Asn Gln Val Pro Gln Tyr Val Leu Ser Leu
305                 310                 315                 320

Leu Arg


<210> SEQ ID NO 14
<211> LENGTH: 322
<212> TYPE: PRT
<213> ORGANISM: Borrelia miyamotoi

<400> SEQUENCE: 14

Met Arg Asn Asn Gly Ile Asn Ala Ala Asn Leu Ser Lys Thr Gln Glu
1               5                   10                  15

Lys Leu Ser Ser Gly Tyr Arg Ile Asn Arg Ala Ser Asp Asp Ala Ala
            20                  25                  30

Gly Met Gly Val Ala Gly Lys Leu Asn Ser Gln Ile Arg Gly Leu Ser
        35                  40                  45

Gln Ala Ser Arg Asn Thr Ser Lys Ala Ile Asn Phe Ile Gln Thr Thr
    50                  55                  60

Glu Gly Asn Leu Asn Glu Val Glu Lys Val Leu Val Arg Met Lys Glu
65                  70                  75                  80

Leu Ala Val Gln Ser Gly Asn Gly Thr Tyr Ser Asp Ser Asp Arg Gly
                85                  90                  95

Ser Ile Gln Ile Glu Ile Glu Gln Leu Thr Asp Glu Ile Asn Arg Ile
            100                 105                 110

Ala Asp Gln Ala Gln Tyr Asn Gln Met His Met Leu Ser Asn Lys Ser
        115                 120                 125

Ala Ala Gln Asn Val Lys Thr Ala Glu Glu Leu Gly Met Gln Pro Ala
    130                 135                 140

Lys Ile Asn Thr Pro Ala Ser Leu Ala Gly Ser Gln Ala Ser Trp Thr
145                 150                 155                 160

Leu Arg Val His Val Gly Ala Asn Gln Asp Glu Ala Ile Ala Val Asn
                165                 170                 175

Ile Tyr Ala Ala Asn Val Ala Asn Leu Phe Asn Gly Glu Gly Ala Gln
            180                 185                 190

Ala Ala Pro Ala Gln Glu Gly Ala Gln Gln Glu Gly Val Gln Ala Val
        195                 200                 205
```

```
Pro Ala Pro Ala Ala Ala Pro Val Gln Gly Gly Val Asn Ser Pro Ile
    210                 215                 220

Asn Val Thr Thr Ala Ile Asp Ala Asn Met Ser Leu Ser Lys Ile Glu
225                 230                 235                 240

Asp Ala Ile Arg Met Val Thr Asp Gln Arg Ala Asn Leu Gly Ala Phe
                245                 250                 255

Gln Asn Arg Leu Glu Ser Val Lys Ala Ser Thr Asp Tyr Ala Ile Glu
            260                 265                 270

Asn Leu Lys Ala Ser Tyr Ala Gln Val Lys Asp Ala Ile Met Thr Asp
        275                 280                 285

Glu Ile Val Ala Ser Thr Thr Asn Ser Ile Leu Thr Gln Ser Ala Met
    290                 295                 300

Ala Met Ile Ala Gln Ala Asn Gln Val Pro Gln Tyr Val Leu Ser Leu
305                 310                 315                 320

Leu Arg


<210> SEQ ID NO 15
<211> LENGTH: 324
<212> TYPE: PRT
<213> ORGANISM: Borrelia turcica

<400> SEQUENCE: 15

Met Arg Asn Asn Gly Ile Asn Ala Ser Asn Leu Ser Lys Thr Gln Glu
1               5                   10                  15

Lys Leu Ser Ser Gly Tyr Arg Ile Asn Arg Ala Ser Asp Asp Ala Ala
            20                  25                  30

Gly Met Gly Val Ala Gly Lys Ile Asn Ala Gln Ile Arg Gly Leu Ser
        35                  40                  45

Gln Ala Ser Arg Asn Thr Ser Lys Ala Ile Asn Phe Ile Gln Thr Thr
    50                  55                  60

Glu Gly Asn Leu Asn Glu Val Glu Lys Val Leu Val Arg Met Lys Glu
65                  70                  75                  80

Leu Ala Val Gln Ser Gly Asn Gly Thr Tyr Ser Asp Ala Asp Arg Gly
                85                  90                  95

Ser Ile Gln Ile Glu Ile Glu Gln Leu Thr Asp Glu Ile Asn Arg Ile
            100                 105                 110

Ala Asp Gln Ser Gln Tyr Asn Gln Met His Met Leu Ser Asn Lys Ser
        115                 120                 125

Ala Ala Gln Asn Val Lys Thr Ala Glu Glu Leu Gly Met Gln Pro Ala
    130                 135                 140

Lys Ile Asn Thr Pro Ala Ser Leu Ser Gly Ala Gln Ala Ser Trp Thr
145                 150                 155                 160

Leu Arg Val His Val Gly Ala Asn Gln Asp Glu Ala Ile Ala Val Asn
                165                 170                 175

Ile Tyr Ala Ala Asn Val Pro Asn Leu Phe Ala Gly Glu Gly Ala Gln
            180                 185                 190

Thr Ala Ala Ala Ala Pro Ala Gln Ala Gly Thr Gln Gln Glu Gly Ala
        195                 200                 205

Gln Glu Pro Ala Ala Ala Ala Ala Pro Ala Gln Gly Gly Val Asn Ser
    210                 215                 220

Pro Val Asn Val Thr Thr Thr Val Asp Ala Asn Met Ser Leu Ala Lys
225                 230                 235                 240

Ile Glu Asn Ala Ile Arg Met Ile Ser Asp Gln Arg Ala Asn Leu Gly
                245                 250                 255
```

-continued

```
Ala Phe Gln Asn Arg Leu Glu Ser Ile Lys Asn Ser Thr Glu Tyr Ser
            260                 265                 270

Ile Glu Asn Leu Lys Ala Ser Tyr Ala Gln Ile Lys Asp Ala Thr Met
        275                 280                 285

Thr Asp Glu Ile Val Ser Ser Thr Thr Asn Ser Ile Leu Thr Gln Ser
    290                 295                 300

Ala Met Ala Met Ile Ala Gln Ala Asn Gln Val Pro Gln Tyr Val Leu
305                 310                 315                 320

Ser Leu Leu Arg


<210> SEQ ID NO 16
<211> LENGTH: 320
<212> TYPE: PRT
<213> ORGANISM: Borrelia hermsii

<400> SEQUENCE: 16

Met Ser Lys Ala Gly Ser Gly Leu Thr Lys Ile Ala Ile Leu Val Asp
1               5                   10                  15

Gly Thr Phe Asp Asp Glu Ser Phe Asn Gly Ser Ala Trp Lys Gly Ala
            20                  25                  30

Lys Lys Val Glu Lys Glu Phe Gly Leu Glu Ile Met Met Lys Glu Ser
        35                  40                  45

Asn Ala Asn Ser Tyr Leu Ala Asp Leu Glu Ser Leu Lys Asn Asn Gly
    50                  55                  60

Ser Asn Phe Leu Trp Leu Ile Gly Tyr Lys Phe Ser Asp Phe Ala Ile
65                  70                  75                  80

Ile Ala Ala Leu Glu Asn Pro Glu Ser Lys Tyr Val Ile Ile Asp Pro
                85                  90                  95

Val Tyr Glu Ser Asp Leu Val Ile Pro Glu Asn Leu Ser Ala Ile Thr
            100                 105                 110

Phe Arg Thr Glu Glu Gly Ala Phe Leu Val Gly Tyr Ile Ala Ala Lys
        115                 120                 125

Met Ser Lys Thr Gly Lys Ile Gly Phe Leu Gly Gly Phe Asp Asp Val
    130                 135                 140

Val Val Asn Thr Phe Arg Tyr Gly Tyr Glu Ala Gly Ala Ile Tyr Ala
145                 150                 155                 160

Asn Lys His Ile Asn Ile Asp Asn Lys Tyr Ile Gly Asn Phe Val Asn
                165                 170                 175

Thr Glu Thr Gly Lys Asn Met Ala Asn Ala Met Tyr Ala Glu Gly Val
            180                 185                 190

Asp Ile Ile Tyr His Val Ala Gly Leu Ala Gly Leu Gly Val Ile Glu
        195                 200                 205

Ser Ala Arg Asp Leu Gly Asp Gly His Tyr Val Ile Gly Val Asp Gln
    210                 215                 220

Asp Gln Ser His Leu Ala Pro Asp Asn Val Ile Thr Ser Ser Ile Lys
225                 230                 235                 240

Asp Ile Gly Arg Val Leu Asn Ile Met Ile Ser Asn Tyr Leu Lys Thr
                245                 250                 255

Asn Ala Phe Glu Gly Gly Gln Val Leu Ser Tyr Gly Leu Lys Glu Gly
            260                 265                 270

Phe Leu Asp Phe Val Lys Asn Pro Lys Met Ile Ser Phe Glu Leu Glu
        275                 280                 285

Lys Glu Leu Asp Asp Leu Ser Glu Gly Ile Ile Asn Gly Lys Ile Ile
    290                 295                 300
```

```
Val Pro Asn Asn Glu Arg Thr Tyr Asn Gln Phe Met Arg Lys Ile Leu
305                 310                 315                 320


<210> SEQ ID NO 17
<211> LENGTH: 202
<212> TYPE: PRT
<213> ORGANISM: Borrelia hermsii

<400> SEQUENCE: 17

Met Phe Leu Phe Ile Ser Cys Asn Asn Gly Gly Pro Glu Leu Lys Gly
1               5                   10                  15

Asn Glu Val Ala Lys Ser Asp Gly Thr Val Leu Asp Leu Ser Lys Ile
            20                  25                  30

Ser Thr Lys Ile Lys Asn Ala Gly Ala Phe Ala Ala Ser Val Gln Glu
        35                  40                  45

Val Ala Thr Leu Val Lys Ser Val Asp Glu Leu Ala Ser Ala Ile Gly
    50                  55                  60

Lys Lys Ile Lys Glu Asp Gly Thr Leu Asp Thr Leu Asn Asn Lys Asn
65                  70                  75                  80

Gly Ser Leu Leu Ala Gly Ala Phe Gln Val Ile Leu Thr Val Glu Ala
                85                  90                  95

Lys Leu Lys Glu Leu Glu Lys Gln Asp Gly Leu Ser Val Glu Leu Arg
            100                 105                 110

Ala Lys Val Thr Ser Ala Lys Ser Ala Ser Ser Gly Leu Val Asn Lys
        115                 120                 125

Leu Lys Gly Gly His Ala Glu Leu Gly Ile Glu Gly Ala Thr Asp Glu
    130                 135                 140

Asn Ala Gln Lys Ala Ile Lys Lys Asp Asn Gly Asp Gln Ser Lys Gly
145                 150                 155                 160

Ala Glu Glu Leu Gly Lys Leu Asn Thr Ala Ile Gly Ala Leu Leu Ser
                165                 170                 175

Ala Ala Asn Asp Ala Val Glu Ala Ala Ile Lys Glu Leu Thr Ala Ala
            180                 185                 190

Pro Ala Lys Pro Ala Thr Pro Ala Lys Pro
        195                 200


<210> SEQ ID NO 18
<211> LENGTH: 337
<212> TYPE: PRT
<213> ORGANISM: Borrelia coriaceae

<400> SEQUENCE: 18

Met Lys Ser Met Lys Pro Lys Leu Leu Met Leu Ile Ile Asn Ile Phe
1               5                   10                  15

Leu Ile Ile Ser Cys Gln Asn Glu Lys Val Ser Met Asn Glu Lys Ser
            20                  25                  30

Pro Leu Ile Ile Ala His Arg Gly Ala Ser Gly Tyr Leu Pro Glu His
        35                  40                  45

Thr Leu Glu Ala Lys Ala Tyr Ala Tyr Ala Leu Gly Ala Asp Tyr Leu
    50                  55                  60

Glu Gln Asp Ile Val Leu Thr Lys Asp Asn Val Pro Ile Ile Met His
65                  70                  75                  80

Asp Ser Glu Leu Asp Thr Thr Thr Asn Val Ala Lys Leu Phe Pro Glu
                85                  90                  95

Arg Ala Arg Glu Asn Gly Lys Tyr Tyr Ala Val Asp Phe Thr Leu Asp
            100                 105                 110
```

```
Glu Ile Lys Ser Leu Ser Ile Ser Glu Arg Phe Asp Pro Glu Thr Arg
        115                 120                 125

Glu Pro Ile Tyr Pro Asn Arg Phe Pro Leu Asn Glu Tyr Asn Phe Lys
    130                 135                 140

Ile Pro Thr Leu Glu Glu Glu Ile Gln Phe Ile Gln Gly Leu Asn Lys
145                 150                 155                 160

Ser Thr Gly Lys Asn Val Gly Ile Tyr Pro Glu Ile Lys Lys Pro Phe
                165                 170                 175

Trp His Lys Gln Gln Gly Lys Asp Ile Ser Lys Ile Val Ile Glu Ile
            180                 185                 190

Leu Asn Gln Tyr Gly Tyr Lys Ser Lys Glu Asp Lys Ile Tyr Leu Gln
        195                 200                 205

Thr Phe Asp Phe Asp Glu Leu Lys Arg Ile Arg Glu Glu Leu Gly Tyr
    210                 215                 220

Gln Gly Lys Leu Ile Met Leu Val Gly Glu Asn Asp Trp Asn Glu Ala
225                 230                 235                 240

Pro Thr Asp Tyr Glu Tyr Ile Lys Ser Gln Glu Gly Met Thr Glu Val
                245                 250                 255

Ala Lys Tyr Ala Asp Gly Ile Gly Pro Trp Ile Ser Gln Ile Ile Ile
            260                 265                 270

Asp Gly Gln Val Thr Asp Leu Ile Ser Leu Ala His Lys His Asn Met
        275                 280                 285

Glu Val His Pro Tyr Thr Phe Arg Ile Asp Ala Leu Pro Ser Tyr Val
    290                 295                 300

Lys Asp Ala Asn Glu Leu Leu Asp Leu Leu Phe Asn Lys Ala Gln Val
305                 310                 315                 320

Asp Gly Ile Phe Thr Asp Phe Val Asp Lys Ala Met Glu Phe Val Lys
                325                 330                 335

Lys


<210> SEQ ID NO 19
<211> LENGTH: 562
<212> TYPE: PRT
<213> ORGANISM: Borrelia coriaceae

<400> SEQUENCE: 19

Met Lys Ser Phe Ser Val Phe Ile Leu Phe Leu Ser Thr Phe Thr Leu
1               5                   10                  15

Ser Cys Lys Phe Tyr Asp Thr Ala Asn Ala Ser Asp Leu Gln Ala Asp
            20                  25                  30

Gly Asp Lys Phe Ser Gln Gly Phe Ser Ser Phe Asn Asp Ile Leu Pro
        35                  40                  45

Phe Ser Asp Leu Lys Ile Asn Lys Asp Val Ser Thr Gly Ser Leu Lys
    50                  55                  60

Ala Gln Gly Thr Ser Ser Ile Lys Gly Asp Glu Lys Lys Gly Lys Gly
65                  70                  75                  80

Thr Ser Lys Asp Pro Ile Lys Asp Gln Glu Ala Ser Gly Leu Lys Gly
                85                  90                  95

Val Gly Val Ala Gly Ala Gly Ala Lys Ser Phe Gly Asp Asp Gly Lys
            100                 105                 110

Lys Glu Glu Val Val Ser Lys Asp Ser Leu Lys Asn Glu Gly Thr Ser
        115                 120                 125

Gly Thr Ala Glu Val Leu Lys Val Ser Lys Glu Val Glu Val Ala Gly
    130                 135                 140
```

-continued

```
Val Asp Thr Ala Lys Pro Ala Gly Gly Asn Gly Glu Glu Val Ala Ser
145                 150                 155                 160

Ile Ser Glu Asn Tyr Leu Gln Asn Gln Glu Thr Leu Val Ala Gln Gly
                165                 170                 175

Ala Gly Val Gly Ser Val Gly Asp Ala Ile Gly Asp Arg Ser Leu Phe
            180                 185                 190

Phe Lys Asn Thr Asp Ser Asn Asn Ala Glu Gln Val Val Ala Thr Glu
        195                 200                 205

Asp Leu Leu Val Gly Ala Ser Glu Gly Val Asn Thr Ser Asp Leu Gly
    210                 215                 220

Leu Lys Val Ala Ile Pro Thr Asp His Val Arg Gly Asp Val Val Ala
225                 230                 235                 240

Thr Glu Thr Gln Asn Ala Glu Lys Lys Gly Asp Lys Thr Gln Asn Thr
                245                 250                 255

Glu Leu Ala Ser Leu Asp Ile Lys Asp Asn Ile Thr Val Asn Val Val
            260                 265                 270

Asp Gly Thr Lys Ile Asn Ile Asn Lys Asn Ser Ser Asn Thr Asn Glu
        275                 280                 285

Ser Ile Asn Val Thr Lys Asp Gly Val Asn Thr Val Ile Lys Gly Val
    290                 295                 300

Glu Thr Ser Ile Lys Thr Ala Asp Gly Lys Val Val Val Lys Lys Arg
305                 310                 315                 320

Thr Leu Lys Lys Gly Leu Lys Lys Lys Asn Ser Lys Lys Gln Ala Ser
                325                 330                 335

Lys Ser Lys Thr Pro Glu Ala Ala Val Val Gly Asn Lys Lys Asn Val
            340                 345                 350

Asp Thr Asn Met Ser Ser Val Ile Gly Leu Asp Ser Glu Ala Leu Gly
        355                 360                 365

Lys Asp Lys Asn Ile Asp Leu Asp Ser Lys Ser Asp Glu Thr Tyr Val
    370                 375                 380

Ile Glu Arg Val Glu Lys Leu Ala Lys Tyr Leu Gln Ser Ala Ile Lys
385                 390                 395                 400

Ile Asn Gly Lys Lys Val Glu Glu Gln Asp Lys Leu Glu Ala Gly Arg
                405                 410                 415

Gln Lys Phe Phe Glu Trp Leu Ser Lys Asn Asp Thr Asp Leu Leu Lys
            420                 425                 430

Arg Lys Ala Leu Val Gln Asp Leu Gln Lys Ile Tyr Asp Leu Met Lys
        435                 440                 445

Asp Lys Ile Ala Asp Ser Thr Glu Leu Gln Asp Trp Phe Gln Ile Val
    450                 455                 460

Ser Asp Asp Ile Gly Asp Glu Glu Thr Asn Ile Ile Asp Val Glu Ser
465                 470                 475                 480

Tyr Tyr Glu Leu Ser Ser Asp Thr Glu Ile Asp Phe Leu Leu Glu Arg
                485                 490                 495

Thr Leu Glu Asp Glu Asn Tyr Ser Gly Phe Ser Ile Ser Leu Phe Met
            500                 505                 510

Gln Ala Leu Ala Asp Thr Leu Tyr Asp Ile Gln Asn Asp Ser His Lys
        515                 520                 525

Ser Gly Glu Glu Ile Leu Gln Glu Leu Lys Arg Val Phe Asp Asp Thr
    530                 535                 540

Phe Tyr Lys Ile Arg Gly Phe Glu Glu Phe Lys Ser Gln Ile Ala Ala
545                 550                 555                 560
```

-continued

```
Glu Asp


<210> SEQ ID NO 20
<211> LENGTH: 193
<212> TYPE: PRT
<213> ORGANISM: Borrelia coriaceae

<400> SEQUENCE: 20

Met Lys Leu Thr Lys Lys Tyr Leu Leu Ala Val Leu Leu Leu Ser Leu
1               5                   10                  15

Ile Asn Cys Asp Leu Leu Ser Lys Asn Lys Ile Leu Thr Ser His Leu
            20                  25                  30

Leu Asn Thr Leu Asp Asn Asn Lys Lys Glu Ala Leu Val Thr Phe Lys
        35                  40                  45

Asn Leu Leu Gln Asp Lys Ser His Leu Glu Tyr Leu Lys Ser Glu Gln
    50                  55                  60

Ala Lys Met Leu Thr Asn Phe Thr Glu Asp Asp Gly Ile Glu Gln Pro
65                  70                  75                  80

His Leu Gln Glu Lys Leu Lys Gly Thr Leu Ser Ser Glu Tyr Asn Glu
                85                  90                  95

Asn Gln Leu Asn Gln Leu Phe Ser Glu Leu Gly Tyr Glu Lys Thr Lys
            100                 105                 110

Gln Phe Leu Asp Asn Leu His Lys Met Leu Gln Ala Ile Lys Asp Gly
        115                 120                 125

Thr Leu Arg Ala Phe His Asp Ser Ser Ser Phe Lys Asp Tyr Asn Thr
    130                 135                 140

Thr Leu Glu Ala Lys Lys Ala Glu Ala Leu Ser Ser Val Lys Lys Glu
145                 150                 155                 160

Leu Tyr Val Gln Tyr Tyr Phe Tyr Ile Asn Asp Leu Gln Thr Ala Asp
                165                 170                 175

Asp Phe Phe Val Leu Thr Arg Asn His Leu Met Ile Phe Lys Asn Asn
            180                 185                 190

Leu
```

SPECIES SPECIFIC ANTIGEN SEQUENCES FOR TICK-BORNE RELAPSING FEVER (TBRF) AND METHODS OF USE

RELATED APPLICATIONS

This application claims the benefit under 35 U.S.C. § 119(e) of U.S. application Ser. No. 15/916,717, filed Mar. 9, 2018, the disclosure of which is incorporated by reference herein in its entirety.

BACKGROUND

Borreliosis is caused by two groups of *Borrelia*, the *B. borgdorferi* group and the Tick-Borne Relapsing Fever (TBRF) *Borrelia* group. It was believed that the *B. borgdorferi* group was the only group that caused Lyme-like symptoms in infected subjects. However, it has been learned that TBRF *Borrelia* also causes Lyme-like symptoms. TBRF *Borrelia* is transmitted by hard (*Ixodes*) and soft (*Ornithodorus*) ticks.

*Borrelia* bacteria that cause TBRF are typically transmitted to humans through the bite of infected "soft ticks" of the genus *Ornithodorus*. Soft ticks differ in two important ways from the more familiar "hard ticks" (e.g., the dog tick and the deer tick). First, the bite of soft ticks is brief, usually lasting less than half an hour. Second, soft ticks do not search for prey in tall grass or brush. Instead, they live within rodent burrows, feeding as needed on the rodent (for example, squirrels, chipmunks and prairie dogs) as it sleeps.

The main symptoms of TBRF are high fever (e.g., 103° F.), headache, muscle and joint aches. Symptoms can reoccur, producing a telltale pattern of fever lasting roughly 3 days, followed by 7 days without fever, followed by another 3 days of fever. Without antibiotic treatment, this process can repeat several times.

Humans typically come into contact with soft ticks when they sleep in rodent-infested cabins. The ticks emerge at night and feed briefly while the person is sleeping. The bites are painless, and most people are unaware that they have been bitten. Between meals, the ticks may return to the nesting materials in their host burrows.

There are several *Borrelia* species that cause TBRF, and these are usually associated with specific species of ticks. For instance, *B. hermsii* is transmitted by *O. hermsi* ticks, *B. parkerii* by *O. parkeri* ticks, and *B. turicatae* by *O. turicata* ticks. Each tick species has a preferred habitat and preferred set of hosts.

Soft ticks can live up to 10 years. Individual ticks will take many blood meals during each stage of their life cycle, and some species can pass the infection along through their eggs to their offspring. The long life span of soft ticks means that once a cabin or homestead is infested, it may remain infested unless steps are taken to find and remove the rodent nest.

Since TBRF can be caused by several species of *Borrelia*, tests need to be comprehensive by including all known species. Also, identification of the *Borrelia* species can aid in identifying the host rodent for eradication. Currently, the standard for identification is by identification of TBRF spirochetes in blood smears of a subject presenting symptoms consistent with TBRF. After obtaining the blood draw the sample must be cultured for at least 24 hours to facilitate identification. However, even early in the disease when spirochetes are highest, positive identification is only made about 70% of the time. (See, www.cdc.gov/relapsing-fever/clinicians/index.html). Thus, prior art materials and methods result in a delay in diagnosis and provide a relatively low level of sensitivity and specificity.

Therefore, what is needed are new materials and methods suitable for the identification of TBRF causative agents with decreased assay time and increased sensitivity and specificity.

SUMMARY OF THE INVENTION

The present invention solves these problems in the prior art by providing antigen-specific amino acid sequences for TBRF *Borrelia* specific species. These novel amino acid sequences are used in assays to identify TBRF specific *Borrelia* in samples from subjects suspected of having TBRF. With the amino acid sequences of the present invention, identification of TBRF *Borrelia* in subject samples is performed with greater speed, sensitivity and specificity than the prior art methods. The amino acid sequences of the present invention can be used in diagnostic and scientific assays. Examples of suitable assays are Immunoblots, ELISA (enzyme-linked immunosorbent assay), etc. The amino acid sequences of the present invention can be used for the detection of TBRF *Borrelia* specific T-cells (e.g., the IgXSPOT test; IGeneX, Palo Alto, Calif.). Further, and importantly, antigens encoded by the amino acid sequences of the present invention can be used in vaccination protocols.

Thus, the present invention contemplates a composition comprising one or more labeled and/or tagged and/or bound amino acid sequences, said amino acid sequences consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20.

The present invention further contemplates that the sequences of the present invention, when bound, are bound to a substance selected from the group consisting of nitrocellulose, nylon, polyvinylidene difluoride (PVDF), magnetic beads and agarose.

The present invention further contemplates that the sequences of the present invention, when tagged, are tagged with an antibody with specificity for said amino acid sequence.

Further, the present invention contemplates a method of detecting *Borrelia* antisera in a sample from a subject suspected of having tick-borne relapsing fever (TBRF), the method comprising: providing a biological sample obtained from a subject suspected of having TBRF, mixing the biological sample with one or more of the labeled, tagged and/or bound amino acid sequences of the present invention and detecting a positive immunobinding reaction which indicates the presence of TBRF antisera in the sample.

The present invention further contemplates that two or more of the labeled and/or tagged and/or bound amino acid sequences of the present invention are mixed with the biological sample. A sample is considered positive for TBRF if at least two amino acid sequences are detected. In another embodiment, a sample is considered positive for TBRF if at least one amino acid sequences is detected.

The present invention further contemplates that the labeled and/or tagged and/or bound amino acid sequences are detected with anti-human IgG antibody linked to a detectable moiety. The present invention contemplates that the detectable moiety may be selected from the group consisting of chromophores, radioactive moieties and enzymes. The present invention contemplates that the detectable moiety may comprise alkaline phosphatase. The present invention contemplates that the detectable moiety may comprise biotin.

The present invention further contemplates a method of detecting and distinguishing various species of *Borrelia* in a sample from a subject suspected of having tick-borne relapsing fever (TBRF), said method comprising: providing a biological sample obtained from a subject suspected of having TBRF, mixing the biological sample with one or more of the labeled and/or tagged and/or bound amino acid sequences of the present invention and detecting a positive immunobinding reaction which indicates the presence of *Borrelia* in the subject, wherein detection of SEQ ID NO: 1, SEQ ID NO: 2, SEQ ID NO: 7, SEQ ID NO: 11, SEQ ID NO: 13, SEQ ID NO: 16 and/or SEQ ID NO: 17 indicates the presence of *B. hermsii*, in the subject; detection of SEQ ID NO: 3, SEQ ID NO: 8, SEQ ID NO: 12 and/or SEQ ID NO: 14 indicates the presence of *B. miyamotoi* in the subject; detection of SEQ ID NO: 4, SEQ ID NO: 5; SEQ ID NO: 9 and/or SEQ ID NO: 15 indicates the presence of *B. turcica* in the subject; detection of SEQ ID NO: 6 and/or SEQ ID NO: 10 indicates the detection of *B. turicatae* in the sample; and, detection of SEQ ID NO: 18, SEQ ID NO: 19 and/or SEQ ID NO: 20 indicates the detection of *B. coriaceae* in the sample. The labeled and/or tagged and/or bound amino acid sequences may be detected with anti-human IgG antibody conjugated to a detectable moiety. The present invention further contemplates that the labeled and/or tagged and/or bound amino acid sequences are detected with anti-human IgG antibody linked to a detectable moiety. The present invention contemplates that the detectable moiety may be selected from the group consisting of chromophores, radioactive moieties and enzymes. The present invention contemplates that the detectable moiety may comprise alkaline phosphatase. The present invention contemplates that the detectable moiety may comprise biotin. The present invention further contemplates that a sample is considered positive for *Borrelia* if at least one amino acid sequence is detected. The present invention further contemplates that a sample is considered positive for a specific species of *Borrelia* if at least one amino acid sequence identified with a specific species is detected.

The present invention contemplates a method of detecting *B. hermsii* in a sample from a subject suspected of having tick-borne relapsing fever (TBRF), said method comprising: providing a biological sample obtained from a subject suspected of having TBRF, mixing the biological sample with one or more of the labeled and/or tagged and/or bound amino acid sequences selected from the group of SEQ ID NO: 1, SEQ ID NO: 2, SEQ ID NO: 7, SEQ ID NO: 11, SEQ ID NO: 13, SEQ ID NO: 16 and/or SEQ ID NO: 17 of claim 1 and detecting a positive immunobinding reaction of SEQ ID NO: 1, SEQ ID NO: 2, SEQ ID NO: 7, SEQ ID NO: 11, SEQ ID NO: 13, SEQ ID NO: 16 and/or SEQ ID NO: 17 the detection of which indicates the presence of *B. hermsii* in the sample.

The present invention contemplates a method of detecting *B. miyamotoi* in a sample from a subject suspected of having tick-borne relapsing fever (TBRF), said method comprising: providing a biological sample obtained from a subject suspected of having TBRF, mixing the biological sample with one or more of the labeled and/or bound amino acid sequences selected from the group of SEQ ID NO: 3, SEQ ID NO: 8, SEQ ID NO: 12 and/or SEQ ID NO: 14 of claim 1 and detecting a positive immunobinding reaction of SEQ ID NO: 3, SEQ ID NO: 8, SEQ NO: 12 and/or SEQ ID NO: 14 which indicates the presence of *B. miyamotoi* in the sample The present invention contemplates a method of detecting *B. turcica* in a sample from a subject suspected of having tick-borne relapsing fever (TBRF), said method comprising: providing a biological sample obtained from a subject suspected of having TBRF, mixing the biological sample with one or more of the labeled and/or tagged and/or bound amino acid sequences selected from the group of SEQ ID NO: 4, SEQ ID NO: 5; SEQ ID NO: 9 and/or SEQ ID NO: 15 of claim 1 and detecting a positive immunobinding reaction of SEQ ID NO: 4, SEQ ID NO: 5; SEQ ID NO: 9 and/or SEQ ID NO: 15 which indicates the presence of *B. turcica* in the sample.

The present invention contemplates a method of detecting *B. turicatae* in a sample from a subject suspected of having tick-borne relapsing fever (TBRF), said method comprising: providing a biological sample obtained from a subject suspected of having TBRF, mixing the biological sample with one or more of the labeled and/or tagged and/or bound amino acid sequences selected from the group of SEQ ID NO: 6 and/or SEQ ID NO: 10 of claim 1 and detecting a positive immunobinding reaction of SEQ ID NO: 6 and/or SEQ ID NO: 10 which indicates the presence of *B. turicatae* in the sample.

The present invention contemplates a method of detecting *B. coriaceae* in a sample from a subject suspected of having tick-borne relapsing fever (TBRF), said method comprising: providing a biological sample obtained from a subject suspected of having TBRF, mixing the biological sample with one or more of the labeled and/or tagged and/or bound amino acid sequences selected from the group of SEQ ID NO: 18, SEQ ID NO: 19 and/or SEQ ID NO: 20 of claim 1 and detecting a positive immunobinding reaction of SEQ ID NO: 18, SEQ ID NO: 19 and/or SEQ ID NO: 20 of claim 1 which indicates the presence of *B. coriaceae* in the sample.

The present invention further contemplates a composition comprising, consisting essentially of or consisting of one or more amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20, and an adjuvant.

The present invention further contemplates a nucleic acid sequence encoding any one or more of the amino acid sequences of the present invention. Said nucleic acid sequence may be labeled.

The present invention further contemplates a method of detecting T cells from a subject having or suspected of having tick-borne relapsing fever (TBRF), the method comprising: providing i) a sample comprising T cells obtained from a subject suspected of having TBRF, ii) a culture apparatus coated at least partially with anti-antibodies specific for one or more cytokines and iii) one or more sequences of claim 1; mixing the blood sample with the one or more of the sequences of claim 1 in the culture apparatus, and detecting any production of the one or more cytokines by the subject's T cells. In one embodiment, the anti-antibodies that are specific for a cytokine are anti-IFNγ antibodies and the cytokine is interferon gamma (IFNγ).

BRIEF DESCRIPTION OF THE FIGURES

FIG. 1 shows an Immunoblot using the TBRF *Borrelia* specific antigenic peptide encoding amino acid sequences of the present invention.

DETAILED DESCRIPTION OF THE INVENTION

The present invention provides novel compositions and methods for diagnosing, treating and vaccinating against infection by Tick-Borne Relapsing Fever causing *Borrelia* sp. The invention is based, in part, on the discovery of species-specific amino acid sequences encoding antigenic peptides (which may also be referred to as peptide antigens or antigens in the art), as described below. Further, the present invention provides nucleic acid sequences encoding the amino acid sequences of the present invention. The nucleic acid sequences may be labeled.

The present invention provides for antigenic amino acid sequences specific for various *Borrelia* species. The amino acid sequences of the present invention encode antigenic peptides that have high specificity and/or sensitivity for the indicated species.

The present invention, in one aspect, is a composition comprising one or more labeled and/or bound amino acid sequences, said amino acid sequences having 90%, 95%, 98%, 99%, 99.5% and/or 100% homology to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20. Sequences less than 100% homologous may have deletions, additions and or substitutions of the 100% homologous sequence. One of ordinary skill in the art can easily determine if sequences less than 100% homologous can bind naturally or non-naturally occurring TBRF-related antibodies as well as the sensitivity and specificity of the antibody to the modified sequences. In other words, one of ordinary skill in the art will be able to identify sequences with significant homology to SEQ ID NOs: 1-20 of the present invention that give acceptable or equivalent responses in the methods of the present invention without undue experimentation, in view of the teachings of this specification.

The present invention, in one aspect, is a composition comprising one or more labeled and/or tagged and/or bound amino acid sequences, said amino acid sequences consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20.

With regard to the present invention, the phrase "a composition comprising one or more labeled and/or tagged and/or bound amino acid sequences, said amino acid sequences consisting of," encompasses a composition having the one or more of the recited sequences and, for example, buffers, labels, etc. In other words, the sequence is limited to the sequence or sequences given but the composition is not limited. The definition specifically excludes amino acids naturally contiguous with a recited sequence being used as a label or tag as an element of the "composition comprising."

In the context of the present invention, a "tagged" amino acid sequence is an amino acid sequence that is attached to a detectable moiety. Non-limiting examples of such "tags" are natural and synthetic (i.e., non-naturally occurring) nucleic acid and amino acid sequences (e.g., poly-AAA tags), antibodies and detectable moieties such as labels (discussed below). Thus, the definitions of the phrases "labeled" and "tagged" may have overlap in that a tag may also, in some instances, function as a label. Further, tags useful with the present invention may be linked to a label.

The amino acid sequences of the present invention, or any tags attached to an amino acid sequence of the present invention, may be labeled with any suitable label known to one of ordinary skill in the art. Such labels may include, but are not limited to, biotin/streptavidin, enzyme conjugates (e.g., horseradish peroxidase (HRP), alkaline phosphatase (AP), glucose oxidase and β-galactosidase), fluorescent moieties (e.g., FITC, fluorescein, rhodamine, etc.), biological fluorophores (e.g., green fluorescent protein, R-phycoerythrin) or other luminescent proteins, etc. Any suitable label known to one of ordinary skill in the art may be used with the present invention.

Further, the amino acid sequences of the present invention may be "bound." A "bound" amino acid sequence is an amino acid sequence that has been immobilized in order to permit the use of the amino acid sequence in a biological test such as, for example, immunoassays. In the context of the present invention, a "bound" amino acid sequence is an amino acid sequence attached (e.g., covalently or non-covalently bound, etc.) directly or indirectly to a non-natural surface or substance. Further still, the "bound" amino acid sequences of the present invention may be attached, directly or indirectly, to a natural surface or substance, either of which is not naturally associated with the amino acid sequence. Non-limiting examples of substances to which the amino acid sequences of the present invention may be bound are nitrocellulose, nylon, polyvinylidene difluoride (PVDF), plastics, metals, magnetic beads and agarose (e.g., beads). Linking agents known to those of ordinary skill in the art may be used to aid or enhance binding of the amino acid sequences of the present invention to a surface or substance.

The present invention, in one aspect, is a composition comprising, consisting essentially of or consisting of one or more labeled and/or tagged and/or bound amino acid sequences, said amino acid sequences consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20 and up to five and up to ten additional amino acids added to one or both of the 3'-prime and 5'-prime ends of the sequence, wherein said additional amino acids may or may not be the naturally contiguous amino acids.

The amino acid sequences of the present invention may be natural occurring and isolated from a natural source. Further, the amino acid sequences of the present invention may be non-natural, synthetic sequences, such as sequences produced by recombinant technology or sequences synthesized by protein synthesizing apparatuses. As such, the amino acid sequences of the present invention may be isolated or may be produced by recombinant technology, as is described and enabled in the literature and in commonly referred to manuals such as, e.g., Short Protocols in Molecular Biology, Second Edition, F. M. Ausubel, Ed., all John Wiley & Sons, N.Y., edition as of 2008; and, Sambrook, et al., Molecular Cloning: A Laboratory Manual, 3rd ed., Cold Spring Harbor Laboratory Press, Cold Spring Harbor, 2001, and as is well known to one of ordinary skill in the art. In one embodiment, the amino acid sequences of the present invention are made recombinantly in *E. coli.*

The amino acid sequences of the present invention may be tagged with an antibody with specificity for any of said amino acid sequences. Specificity for said amino acid sequence, i.e., antibody specificity, is the property of antibodies which enables them to react preferentially with some antigenic determinants and not with others. Specificity is dependent on chemical composition, physical forces and molecular structure at the binding site. Sensitivity is how strongly the antibody binds to the antigenic determinant. One of ordinary skill in the art can easily determine specificity and sensitivity of an antibody for a particular amino acid sequence using standard affinity assays, such as immunoblotting, Ouchterlony assays, titer assays, etc.

In another aspect, the present invention provides a method of quickly and accurately detecting *Borrelia* antisera in a sample from a subject suspected of having tick-borne relapsing fever (TBRF). A subject suspected of having TBRF can be identified as having symptoms such as a high fever (e.g., 103° F.), headache, muscle and joint aches. Symptoms typically reoccur, producing a telltale pattern of fever lasting roughly 3 days, followed by approximately 7 days without fever, followed by another 3 days of fever. Without proper antibiotic treatment, this process can repeat several times. Since the symptoms of TBRF can mimic, for example, viral flu-like symptoms, accurate diagnosis of TBRF is important for providing an effective treatment for the subject. The present invention provides a quick and easy diagnostic test for detecting the presence of antibodies specific for the causative *Borrelia* species, thereby satisfying the need for such a test.

The method of the present invention for detecting *Borrelia* antisera in a sample from a subject suspected of having TBRF, may comprise, for example, providing a biological sample (e.g., blood, saliva) obtained from a subject suspected of having TBRF, mixing the biological sample with one or more of the labeled and/or bound amino acid sequences of the present invention and detecting a positive reaction which indicates the presence of TBRF antisera in the sample. The antisera may be detected by, for example, immunoblotting, Elispot, ELISA, Western blotting or any other appropriate immunoassay known to one of ordinary skill in the art. These techniques are known to one of ordinary skill in the art and procedures can be found in common technical references. While similar, each of these techniques has its advantages and disadvantages. Other suitable techniques may be known to those of skill in the art and are incorporated herein.

Briefly, Western blotting can involve separating proteins by electrophoresis and then transferring to nitrocellulose or other solid media (e.g., polyvinylidene fluoride or PVDF-membrane and nylon membrane), and is described in more detail below. Immunoblotting can also involve applying proteins to a solid media manually or by machine. Preferably, the proteins are applied in straight lines or spots and dried, binding them to the solid support medium, e.g., nitrocellulose. The proteins used in an immunoblot can be isolated from biological samples or produced by recombinant technology, as is well known by those of ordinary skill in the art. The bound proteins are then exposed to a sample or samples suspected of having antibodies specific for the target proteins.

With this procedure, a known antibody can be used to determine if a protein is present in a sample, such as when the proteins of lysed cells are separated by electrophoresis and transferred to the solid medium. Western blotting allows for the identification of proteins by size as well as by specificity for a specific antibody.

Similarly, with a procedure called immunoblotting, known proteins can be bound to the solid medium and samples, such as samples from subjects suspected of having an infection, can be tested for the presence of specific antibodies in the sample by contacting the bound protein with the sample. An antibody that binds the target protein is usually referred to as the primary antibody. A secondary antibody, specific for conserved regions of the primary antibody (for example, a rabbit-anti-human IgG antibody may be used to detect primary human antibodies) is used to detect any bound primary antibodies. The secondary antibody is usually labeled with a detectable moiety for visualization. Non-limiting examples of suitable labels include, for example, chromophores such as biotin, radioactive moieties and enzymes such as alkaline phosphatase, etc. The use of these and other materials for the visualization of antibodies are well known to one of ordinary skill in the art.

The Enzyme-Linked ImmunoSpot (ELISPOT) method can detect human T cells that respond to TBRFspecific antigens in vitro. In an ELISPOT assay, the surfaces of PVDF membrane in a 96-well microtiter plate are coated with capture antibody that binds, for example, anti-Interferon gamma (IFNγ) or other cytokine-specific antibody. During the cell incubation and stimulation step, the T cells isolated from patient whole blood are seeded into the wells of the plate along with aforementioned sequence(s), and form substantially a monolayer on the membrane surface of the well. Upon stimulation of any antigen-specific cells with one or more of the sequences of the present invention they are activated and they release the IFNγ, which is captured directly on the membrane surface by the immobilized antibody. The IFNγ is thus "captured" in the area directly surrounding the secreting cell, before it has a chance to diffuse into the culture media, or to be degraded by proteases and bound by receptors on bystander cells. Subsequent detection steps visualize the immobilized IFNγ as an ImmunoSpot; essentially the secretory footprint of the activated cell.

For a specific example of an ELISPOT test, each well of the plate is coated with a purified cytokine-specific antibody specific for the test or cell being detected. Subject's (i.e., a subject suspected of having TBRF) T cells are isolated and cultured in each well and stimulated with recombinant antigens of one or more sequences of the present invention. TBRF-positive patient cells secrete cytokine in response to stimuli, which is captured by the antibody coated in the well and further detected by ELISA.

ELISA assays are also used to detect antigens. The ELISA assay can permit the quantification of a specific protein in a mix of proteins (for example, a lysate) or determine if a peptide is present in a sample. Likewise, ELISA assays can be used to determine if a specific antibody is present by using a specific antigen as a target. As used with the present invention, target amino acid sequence(s) are attached to a surface. Then, if present in the sample being tested, the reactive antibody can bind to the antigen. A secondary antibody linked to an enzyme is added, and, in the final step, a substance containing the enzyme's substrate is added. The subsequent reaction produces a detectable signal, most commonly a color change in the substrate.

In one aspect of the method of the present invention, a positive result is indicated when two or more of the labeled and/or bound amino acid sequences of the present invention are mixed with the biological sample and when at least two amino acid sequences are detected. In another aspect of the invention, a positive result is indicated when at least one of the labeled and/or bound amino acid sequences of the present invention are mixed with the biological sample and when at least one amino acid sequence is detected.

In the method of the present invention, any primary antibody bound to a peptide encoded by an amino acid sequence of the present invention may be detected with anti-human antibodies, such as IgG or IgM, used as the secondary antibody conjugated to a detectable moiety. As discussed above, the detectable moiety may be selected from the group consisting of chromophores, radioactivity moieties and enzymes or other detectable moiety known to one of ordinary skill in the art. In one embodiment, the detectable moiety comprises alkaline phosphatase. In another embodiment the detectable moiety comprises biotin.

In another aspect of the invention, a method is provided for detecting and distinguishing various species of *Borrelia* in a sample. The sample may be from a subject suspected of having TBRF. The method may comprise, for example, providing a sample, for example, a biological sample obtained from a subject suspected of having TBRF and mixing or contacting the biological sample with one or more of the labeled and/or bound amino acid sequences of the present invention. Amino acids may be labeled to confirm their presence if positive results are not obtained in the assay. The detection of a positive immunobinding reaction indicates the presence of *Borrelia* in the sample, wherein detection of SEQ ID NO: 1, SEQ ID NO: 2, SEQ ID NO: 7, SEQ ID NO: 11, SEQ ID NO: 13, SEQ ID NO: 16 and/or SEQ ID NO: 17 indicates the presence of *B. hermsii*, in the sample; detection of SEQ ID NO: 3, SEQ ID NO: 8, SEQ ID NO: 12 and/or SEQ ID NO: 14 indicates the presence of *B. miyamotoi* in the sample; detection of SEQ ID NO: 4, SEQ ID NO: 5; SEQ ID NO: 9 and/or SEQ ID NO: 15 indicates the presence of *B. turcica* in the sample, detection of SEQ ID NO: 6 and/or SEQ ID NO: 10 indicates the detection of *B. turicatae* in the sample and, detection of SEQ ID NO: 18, SEQ ID NO: 19 and/or SEQ ID NO: 20 indicates the detection of *B. coriaceae* in the sample. The assay used may be any of the assays described elsewhere in this specification, or as are known to one of ordinary skill in the art.

In a preferred embodiment of the invention, a sample is considered positive for *Borrelia* if at least two amino acid sequences are detected. A sample is considered positive for a specific species of *Borrelia* if at least two amino acid sequences identified with a species are detected. In another embodiment of the invention, a sample is considered positive for *Borrelia* if at least one amino acid sequence is detected. A sample is considered positive for a specific species of *Borrelia* if at least one amino acid sequence identified with a species is detected.

In another aspect of the invention, a method is provided for detecting and distinguishing various species of *B. hermsii* in a sample. The sample may be from a subject suspected of having TBRF. The method may comprise, for example, providing a sample, for example, a biological sample obtained from a subject suspected of having TBRF and mixing or contacting the biological sample with one or more of the labeled and/or bound amino acid sequences of the present invention specific for *B. hermsii*. The detection of a positive immunobinding reaction of SEQ ID NO: 1, SEQ ID NO: 2, SEQ ID NO: 7, SEQ ID NO: 11, SEQ ID NO: 13, SEQ ID NO: 16 and/or SEQ ID NO: 17 indicates the presence of *B. hermsii*, in the sample. The assay used may be any of the assays described elsewhere in this specification, or as are known to one of ordinary skill in the art. A sample is considered positive for *B. hermsii* if at least one amino acid sequence is detected.

In another aspect of the invention, a method is provided for detecting and distinguishing various species of *B. miyamotoi* in a sample. The sample may be from a subject suspected of having TBRF. The method may comprise, for example, providing a sample, for example, a biological sample obtained from a subject suspected of having TBRF and mixing or contacting the biological sample with one or more of the labeled and/or bound amino acid sequences of the present invention. The detection of, for example, a positive immunobinding reaction of SEQ ID NO: 3, SEQ ID NO: 8, SEQ ID NO: 12 and/or SEQ ID NO: 14 indicates the presence of *B. miyamotoi* in the sample. The assay used may be any of the assays described elsewhere in this specification, or as are known to one of ordinary skill in the art. A sample is considered positive for *B. miyamotoi* if at least one amino acid sequence is detected.

In another aspect of the invention, a method is provided for detecting and distinguishing various species of *B. turcica* in a sample. The sample may be from a subject suspected of having TBRF. The method may comprise, for example, providing a sample, for example, a biological sample obtained from a subject suspected of having TBRF and mixing or contacting the biological sample with one or more of the labeled and/or bound amino acid sequences of the present invention. The detection of, for example, a positive immunobinding reaction of SEQ ID NO: 4, SEQ ID NO: 5; SEQ ID NO: 9 and/or SEQ ID NO: 15 indicates the presence of *B. turcica* in the sample. The assay used may be any of the assays described elsewhere in this specification, or as are known to one of ordinary skill in the art. A sample is considered positive for *B. turcica* if at least one amino acid sequence is detected.

In another aspect of the invention, a method is provided for detecting and distinguishing various species of *B. turicatae* in a sample. The sample may be from a subject suspected of having TBRF. The method may comprise, for example, providing a sample, for example, a biological sample obtained from a subject suspected of having TBRF and mixing or contacting the biological sample with one or more of the labeled and/or bound amino acid sequences of the present invention. The detection of, for example, a positive immunobinding reaction of SEQ ID NO: 6 and/or SEQ ID NO: 10 indicates the detection of *B. turicatae* in the sample. The assay used may be any of the assays described elsewhere in this specification, or as are known to one of ordinary skill in the art. A sample is considered positive for *B. turicatae* if at least one amino acid sequence is detected.

In another aspect of the invention, a method is provided for detecting and distinguishing various species of *B. coriaceae* in a sample. The sample may be from a subject suspected of having TBRF. The method may comprise, for example, providing a sample, for example, a biological sample obtained from a subject suspected of having TBRF and mixing or contacting the biological sample with one or more of the labeled and/or bound amino acid sequences of the present invention. The detection of, for example, a positive immunobinding reaction of SEQ ID NO: 18, SEQ ID NO: 19 and/or SEQ ID NO: 20 indicates the detection of *B. coriaceae* in the sample. The assay used may be any of the assays described elsewhere in this specification, or as are known to one of ordinary skill in the art. A sample is considered positive for *B. coriaceae* if at least one amino acid sequence is detected.

In another aspect of the present invention the amino acid sequences of the present invention may be used as vaccines in vaccination protocols. Vaccination protocols are well known to one of ordinary skill in the art. Briefly, vaccination is the administration of antigenic material (a vaccine) to stimulate an individual's immune system to develop adaptive immunity to a pathogen. Vaccines can prevent or ameliorate morbidity from infection.

Vaccines are typically administered with adjuvants. Adjuvants are compounds and mixtures of compounds designed or found to aid in stimulation of the immune system. For example an adjuvant is a pharmacological or immunological agent that modifies the effect of other agents. Adjuvants may be added to a vaccine to modify the immune response by boosting it such as to produce a greater quantity of antibodies and provide longer-lasting protection, thus minimizing the amount of injected foreign material. Adjuvants may also be used to enhance the efficacy of a vaccine by helping to modify the immune response to particular types of immune system cells. There are different classes of adjuvants that can skew immune responses in different directions. For example, adjuvants may selectively skew the immune response by preferentially activating T cells or B cells depending on the purpose of the vaccine. Adjuvants may also be used in the production of antibodies from immunized animals. For example, rabbit anti-human IgG antibodies may be produced by inoculating a rabbit with conserved portions of a human IgG antibody in combination with an adjuvant. The most commonly used adjuvants include aluminum hydroxide, paraffin oil and Freud's complete and incomplete adjuvant.

Although not fully understood adjuvants are believed to apply their effects through different mechanisms. Some adjuvants, such as alum, function as delivery systems by generating depots that trap antigens at the injection site, providing a slow release that continues to stimulate the immune system. Other adjuvants augment or stimulation the host immune response by providing a general boost to the immune system.

In this regard, another aspect of the present invention is a composition comprising or consisting essentially of one or more amino acid sequences, said amino acid sequences having 90%, 95%, 98%, 99%, 99.5% and/or 100% homology selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20 and an adjuvant. The adjuvant may be any adjuvant known to one of ordinary skill in the art suitable for use in humans. Combinations two or more adjuvants may be used. One of ordinary skill in the art will be able to identify sequences of the present invention that give acceptable or equivalent immunological responses without undue experimentation. By definition, with regard to the phrase "consisting essentially of," agents other than the recited sequences and adjuvant are not considered essential in the context of the present invention.

Isolated nucleic acid sequences, including polynucleotides and oligonucleotides, encoding the amino acid sequences of the present invention, and portions thereof, may be expressed in cultured cells to provide isolatable quantities of peptides displaying biological (e.g., immunological) properties of the antigenic peptide encoded by the amino acid sequences of the present invention. Because of redundancy of the genetic code, multiple nucleic acid sequences may be suitable for the production of the peptide sequences of the present invention. One of ordinary skill in the art will be able to determine one or more nucleic acid sequences for the production of the amino acid sequences of the present invention. The nucleic acid sequences encoding the amino acid sequences of the present invention may be labeled by any suitable label known to one of ordinary skill in the art.

In this regard, nucleic acid sequences of suitable for the production of the amino acid sequences of the present invention may be substantially homologous to the naturally occurring sequences. Substantial homology of a nucleic acid sequence means either that (a) there is greater than about 65%, typically greater than about 75%, more typically greater than about 85%, preferably greater than about 95%, and more preferably greater than about 98% homology, most preferably 99% with the naturally occurring sequence or (b) the homologous nucleic acid sequence will hybridize to the compared sequence or its complementary strand under stringent conditions of the temperature and salt concentration. These stringent conditions will generally be a temperature greater than about 22° C., usually greater than about 30° C. and more usually greater than about 45° C., and a salt concentration generally less than about 1 M, usually less than about 500 mM, and preferably less than about 200 mM. The combination of temperature and salt concentration is more important in defining stringency than either the temperature or the salt concentration alone. Other conditions which affect stringency include GC content of the compared sequence, extent of complementarity of the sequences, and length of the sequences involved in the hybridization, as well as the composition of buffer solution(s) used in the hybridization mixture. These and other factors affecting stringency are well described in the scientific and patent literature. One of ordinary skill in the art will be able to determine suitable conditions for determining the homology of the nucleic acid sequences encoding the antigenic peptides of the present invention.

Further, homologous nucleic acid sequences may be determined based on the nature of a nucleotide substitution in the nucleic acid sequence. For example, conservative nucleotide substitutions will be tolerated better and, therefore, can be more numerous in a particular nucleic acid sequence than non-conservative nucleotide substitutions. One or ordinary skill in the art will be able to determine the suitable number and location of substitutions that may be allowed in a nucleic acid sequence that encodes an amino acid sequence of the present invention without adversely affecting the species specificity of the encoded antigenic peptide, without undue experimentation.

The present invention will now be described in view of the following, non-limiting, exemplification.

EXEMPLIFICATION

Example 1

Borreliosis is caused by two groups of *Borrelia, B. burgdorferi* group and the Tick-Borne Relapsing Fever (TBRF) *Borrelia* group. It was believed that *B. burgdorferi* group is the only group that causes Lyme-like symptoms. However it is now known that TBRF *Borrelia* can also cause Lyme-like symptoms. TBRF *Borrelia* can be transmitted by hard (*Ixodes*) and soft (*Ornithodorus*) ticks.

TBRF ImmunoBlot

The TBRF *Borrelia* immunoblot of the present invention is designed to detect antibodies to TBRF *Borrelia* species [including, but not limited to *Borrelia miyamotoi, B. hermsii, B. turicatae* and *B. coriaceae*] specific antigens in human serum. For diagnostic purposes, immunoblot test results may be used in conjunction with clinical symptoms and other evidence available to the diagnosing physician.

The TBRF *Borrelia* ImmunoBlot Test is a qualitative immunoblot assay that detects antibodies directed against TBRF associated *Borrelia* species in sera of patients suspected of having TBRF *Borrelia* infection. Recombinant TBRF *Borrelia* antigens (protein sequences listed below) were applied as straight lines onto nitrocellulose strips, where they bind. The strips were then be used in the TBRF *Borrelia* ImmunoBlot Test.

Species specific *Borrelia* amino acid sequences of the present invention:

*B. hermsii* - BipA-1H

[SEQ ID NO: 1]

MSESNWEIDEPGSVQDIRNSVASELQKPENIGQRGKSVGKEVGKDAAASGEGAVVAVGSKQN

TLQNSENSSQEGAGSALQKPGDSPQKGVASQEGTNGALQGVVAAGGVSVGGSGVGAAASD

GNSSSSQEAESVDLKNVLADSHGVGASNLNIKAEGDISTGHGTEGVIASGDLTNTIITSGVTAAA

SPAIVSGDERGVAAIKDSIAVVLETQKEAQKETEKETENVKFAVLGTVKKIVDGVADGIANVIEYG

LENGID

*B. hermsii* - BipA-2H

[SEQ ID NO: 2]

MNKVKDGIKTASKGAETFVTAAMQGAGAVLGSLQDVGNFVMDATLSMGDMFAGIKSDSDVSS

ANSGMTVNSGMTVSLSSNETQVIGHLEEYLKSAIKVNGNESSRQSKLENGRQKFFAWLREKDT

DFSKRKELVQAMQRVYNFIKEKSSNSRELQTWVLGVVGDDDTVVDVDRDDELNSDVEIDFLIK

KTLSSRDYSGFAVSLLFQALADTLYDAENDRDKPEEQIFKDLKAVFSDNAGEDKGFGEFKSIIED

KSQA

*B. miyamotoi* - BipA

[SEQ ID NO: 3]

MAKAGNFDEVLDLDGDDEEAEIDEIEQNLSEGVDGNIDQNPGNVDGHIVLVDAQGVSVPTVVE

HSAVSSSVERRVVTVGQNVESRRLTKVERLEKYLESAIKSGGKLNEQQRRLKNGKQMLFTWL

NEDANASKRAELEQDMQKLYGLIKESITDSSSQFSSRDGEYSDEAIDGLLNSLFSSSFDNTFAL

DLFFQALLNTLCDFKKDNCKDEEVIFADIRKVFSDESDTKGHFGYLKSKLKDELVISDEGDYGED

EDFEED

*B. turcica* - BipA1

[SEQ ID NO: 4]

MEEEASIESEAMPLDEAKISSLDKETVPAVQADGTPEQIVASVGLEGEESKKFEHLKGSLGDAIK

VNGKGEEKRKENEERQKEFFDWLDKNDPDLSKRKELAELMKKVYGLLKEHAQNSEQIKSFVE

GTPKDENVKKIGVTSARDIKTDEQVEALIKAVLGHSEESGTNLSLFFQKLGDAFGTEDGESQKS

NEKILEELKRVCESSDEIKKLKEDLKIEEKVQS

*B. turcica* - BipA2

[SEQ ID NO: 5]

MNIDAVADLLADQQEAASTGLKDASTGLKDTSTGLSKLDKKEKKVSSLKETLENSSNVLYESSS

PTKTRQEEFFKWLEENDSDYSKRKQLEESMDKVFSLIKDSASSSTEIKEIIAKGQSDAGIIKAGIK

TADDIKTDEQVDALVKFVTGTGDDLDLESGSSSIKAFFGTLAEVFDDDLNDVMTDKKGQKRGH

DKVFEDLKKVFSEDSDGPFDILKDALKQALKNN

*B. turicatae* - BipA-1H

[SEQ ID NO: 6]

MSTSYWSVDNDGFVQGTKSFVDSPLRKPDRFDQEVSAGGKKIEKAVSRNLRVAGGQRQGIAD

DGIGVAGVREAGGVLKDAGNAVQRDINGSGEGIKNDVIQNPEGVGVQVAVGSADTGADSGQE

AGKVFQNLGDTGTQSIQRVVSSSDLNSDLGVGSKDGISTNGMSTNHVTENENSINSITSTSSGL

NTALQMAGTSTRTSGYEGEITTNTQDRTFVETGTQDSKAQYSDFSDQDIRDKVLGSVVGGVV

-continued

*B. hermsii* - GlpQ-s

[SEQ ID NO: 7]

MASMTGGQQMGRGSEKMSQNQKSPLVIAHRGASGYLPEHTLEAKAYAYALGADYLEQDIVLT

KDNIPVIMHDPELDTTTNVAKLFPERARENGRYYSVDFTLDELKSLSLSERFDPASRNPIYPNRF

PLNEHDFKIPTLEEEIQFIQGLNKSTGRNVGIYPEIKKPLWHKQQGKDISKIVIEILNKYGYKSKED

KIYLQTFDFDELKRIREELGYQGKLIMLVGENDWDEAPTDYEYIKSEEGMAEVAKYSDGIGPWIP

QIIIEGKITDLTSLAHKHNMEVHPYTFRIDALPSYVKDADELLDLLFNKAKVDGIFTDFTDTVVNFIT

KIKPKGE

*B. miyamotoi* - GlpQ-s

[SEQ ID NO: 8]

MASMTGGQQMGRGSEMGENKKSPLIIAHRGASGYLPEHTLEAKAYAYALGADYLEQDIVLTKD

NIPVIMHDPEIDTTTNVAQLFPNRARENGRYYATDFTLTELKSLNLSERFDPENKKPIYPNRFPL

NEYNFKIPTLEEEIQFIQGLNKSTGKNVGIYPEIKKPFWHKQQGKDISKIVIEILNKYGYKSKEDKI

YLQTFDFDELKRIRKELGYQGKLIMLVGENDWNEAPTDYEYIKSEEGIAEVAKYSDGIG

*B. turcica* - GlpQ

[SEQ ID NO: 9]

MASMTGGQQMGRGSKVSMNKALPLVIAHRGASGYLPEHTLEAKAFAYALGAHYLEQDIVLTKD

DIPIIMHDPEIDTTTNVAEIFPERARKDGRYYSVDFTLRELKSLKLSERFDPKTGKPIYPNRFPLN

EYNFKIPTLEEEIQFIQGLNKSTGRNVGIYPEIKKPFWHKQQGKDISKIVIEMLNKYGYKSKEDKIY

LQIFDFDELKRIREELGYKGKLVMLIGENDWNEAPTDYEYIKSEEGIAEVAKYSDGIGPWIPQVII

DGKVTGLTSLAHKHKMEVHPYTMRIDALPSYVKDANELLNLLFNKAKVDGVFTDFPDVVLGFIR

K

*B. turicatae* - GlpQ

[SEQ ID NO: 10]

MASMTGGQQMGRGSEKMSMTNKKPPLIIAHRGASGYLPEHTLEAKAFAYALGADYLEQDIVLT

KDNVPIIMHDPELDTTTNVAKLFPERARENGRYYSVDFTLDELKSLSLSERFDLETRKPIYPNRF

PLNEYNVKIPTLEEEIQFIQGLNKSTGRNVGIYPEIKKPLWHKQQGKDISKIVIEILNKYGYKSKED

KIYLQTFDFDELKRIREELGYQGKLIMLVGENDWDEAPTDYEYIKSQEGMTEVAKYADGIGPWI

PQIIIDGKITDLTSLAHKYNMEVHAYTFRIDSLPSYVKDANELLDLLFNKAKIDGLFTDFTDTVVKF

VKQ

*B. hermsii* - BpcA

[SEQ ID NO: 11]

MASMTGGQQMGRGSSDANLLKTLDNNQKQALIYFKDTLQDKKYLNDLTASQKNFLDDLEKNK

KDPGLQDKLKKTLSSEYDGSQFNKLLNELGNAKVKQFLQQLHIMLQSIKDGTLTSFSYANFKDL

QTLEQKKERALQYINGRLYVEYYFYINGISNADNFFESVMQLLET

*B. miyamotoi* - BpcA

[SEQ ID NO: 12]

MLDHNLQPNKINNIISSLDSNQKQALIFFKNLVKNKQYSKDLEQASKSYLENLKEKNNQNLNLQN

KLNQGLNCDYDDSKIEKLFDQLGNDKMKKFLQQLHLMLKSINDGTLISFSSSNFRDTTTLSQKK

EKALEYIKSQLYIEFYFHSNDISDTEFFFQRTIALLETQN

*B. hermsii* - P41

[SEQ ID NO: 13]

MRNNSINATNLSKTQEKLSSGHRINRASDDAAGMGVAGKINAQIRGLSQASRNTSKAINFIQTT

EGNLNEVERVLVRMKELAVQSGNGTYSDADRGSIQIEIEQLTDEINRIADQAQYNQMHMLSNKS

AAQNVKTAEELGMQPAKINTPASLAGSQASWTLRVHVGANQDEAIAVNIYASNVANLFAGEGA

-continued

QAAPVQEIGQQEEGQAAPAPAAAPAQGGVNSPINVTTAVDANMSLAKIEGAIRMVSDQRANLG

AFQNRLESIKDSTEYAIENLKASYAQIKDATMTDEVVASTTHSILTQSAMAMIAQANQVPQYVLS

LLR

*B. miyamotoi* - P41

[SEQ ID NO: 14]

MRNNGINAANLSKTQEKLSSGYRINRASDDAAGMGVAGKLNSQIRGLSQASRNTSKAINFIQTT

EGNLNEVEKVLVRMKELAVQSGNGTYSDSDRGSIQIEIEQLTDEINRIADQAQYNQMHMLSNKS

AAQNVKTAEELGMQPAKINTPASLAGSQASWTLRVHVGANQDEAIAVNIYAANVANLFNGEGA

QAAPAQEGAQQEGVQAVPAPAAAPVQGGVNSPINVTTAIDANMSLSKIEDAIRMVTDQRANLG

AFQNRLESVKASTDYAIENLKASYAQVKDAIMTDEIVASTTNSILTQSAMAMIAQANQVPQYVLS

LLR

*B. turcica* - P41

[SEQ ID NO: 15]

MRNNGINASNLSKTQEKLSSGYRINRASDDAAGMGVAGKINAQIRGLSQASRNTSKAINFIQTT

EGNLNEVEKVLVRMKELAVQSGNGTYSDADRGSIQIEIEQLTDEINRIADQSQYNQMHMLSNKS

AAQNVKTAEELGMQPAKINTPASLSGAQASWTLRVHVGANQDEAIAVNIYAANVPNLFAGEGA

QTAAAAPAQAGTQQEGAQEPAAAAAPAQGGVNSPVNVTTTVDANMSLAKIENAIRMISDQRAN

LGAFQNRLESIKNSTEYSIENLKASYAQIKDATMTDEIVSSTTNSILTQSAMAMIAQANQVPQYVL

SLLR

*B. hermsii* - BmpA10

[SEQ ID NO: 16]

MSKAGSGLTKIAILVDGTFDDESFNGSAWKGAKKVEKEFGLEIMMKESNANSYLADLESLKNN

GSNFLWLIGYKFSDFAIIAALENPESKYVIIDPVYESDLVIPENLSAITFRTEEGAFLVGYIAAKMSK

TGKIGFLGGFDDVVVNTFRYGYEAGAIYANKHINIDNKYIGNFVNTETGKNMANAMYAEGVDIIY

HVAGLAGLGVIESARDLGDGHYVIGVDQDQSHLAPDNVITSSIKDIGRVLNIMISNYLKTNAFEG

GQVLSYGLKEGFLDFVKNPKMISFELEKELDDLSEGIINGKIIVPNNERTYNQFMRKIL

*B. hermsii* - OspC10

[SEQ ID NO: 17]

MFLFISCNNGGPELKGNEVAKSDGTVLDLSKISTKIKNAGAFAASVQEVATLVKSVDELASAIGK

KIKEDGTLDTLNNKNGSLLAGAFQVILTVEAKLKELEKQDGLSVELRAKVTSAKSASSGLVNKLK

GGHAELGIEGATDENAQKAIKKDNGDQSKGAEELGKLNTAIGALLSAANDAVEAAIKELTAAPA

KPATPAKP

*B. coriaceae* - GlpQ

[SEQ ID NO: 18]

MKSMKPKLLMLIINIFLIISCQNEKVSMNEKSPLIIAHRGASGYLPEHTLEAKAYAYALGADYLEQDI

VLTKDNVPIIMHDSELDTTTNVAKLFPERARENGKYYAVDFTLDEIKSLSISERFDPETREPIYPNRF

PLNEYNFKIPTLEEEIQFIQGLNKSTGKNVGIYPEIKKPFWHKQQGKDISKIVIEILNQYGYKSKEDK

IYLQTFDFDELKRIREELGYQGKLIMLVGENDWNEAPTDYEYIKSQEGMTEVAKYADGIGPWISQIII

DGQVTDLISLAHKHNMEVHPYTFRIDALPSYVKDANELLDLLFNKAQVDGIFTDFVDKAMEFVKK

*B. coriaceae* - BIPA

[SEQ ID NO: 19]

MKSFSVFILFLSTFTLSCKFYDTANASDLQADGDKFSQGFSSFNDILPFSDLKINKDVSTGSLKA

QGTSSIKGDEKKGKGTSKDPIKDQEASGLKGVGVAGAGAKSFGDDGKKEEVVSKDSLKNEGT

SGTAEVLKVSKEVEVAGVDTAKPAGGNGEEVASISENYLQNQETLVAQGAGVGSVGDAIGDR

SLFFKNTDSNNAEQVVATEDLLVGASEGVNTSDLGLKVAIPTDHVRGDVVATETQNAEKKGDK

TQNTELASLDIKDNITVNVVDGTKININKNSSNTNESINVTKDGVNTVIKGVETSIKTADGKVVVK

-continued

KRTLKKGLKKKNSKKQASKSKTPEAAVVGNKKNVDTNMSSVIGLDSEALGKDKNIDLDSKSDE

TYVIERVEKLAKYLQSAIKINGKKVEEQDKLEAGRQKFFEWLSKNDTDLLKRKALVQDLQKIYDL

MKDKIADSTELQDWFQIVSDDIGDEETNIIDVESYYELSSDTEIDFLLERTLEDENYSGFSISLFM

QALADTLYDIQNDSHKSGEEILQELKRVFDDTFYKIRGFEEFKSQIAAED

*B. coriaceae* - BPCA

[SEQ ID NO: 20]

MKLTKKYLLAVLLLSLINCDLLSKNKILTSHLLNTLDNNKKEALVTFKNLLQDKSHLEYLKSEQAK

MLTNFTEDDGIEQPHLQEKLKGTLSSEYNENQLNQLFSELGYEKTKQFLDNLHKMLQAIKDGTL

RAFHDSSSFKDYNTTLEAKKAEALSSVKKELYVQYYFYINDLQTADDFFVLTRNHLMIFKNNL

ImmunoBlotting:

Immunoblotting is well known to one of ordinary skill in the art. With regard to the present invention, to perform the TBRF *Borrelia* ImmunoBlot test, patient serum was incubated with TBRF *Borrelia* ImmunoBlot strips, produced as described above, in each trough of an incubation tray. If specific antibodies to TBRF *Borrelia* antigens were present in a sample, they were bound to the corresponding antigen bands. After washing away unbound antibodies, the bound TBRF *Borrelia* specific antibodies were detected with alkaline phosphatase (AP) conjugated goat or rabbit anti-human IgG or IgM antibody. After removing the unbound conjugated antibody, the strips were incubated with BCIP/NBT, an AP chromogenic substrate. A dark purple colored precipitate developed on the antigen-antibody complexes. Bands were visualized and scored for intensity relative to the positive, negative and calibrator (calibration) controls.

Example 2

Specificity of TBRF *Borrelia* ImmunoBlot

Method:

TBRF ImmunoBlot strips were tested with rabbit anti-TBRF *Borrelia* serum samples and *Borrelia burgdorferi* serum samples. Rabbit antibodies to the following *Borrelia* species were tested: *B. hermsii*, TBRF *Borrelia* species, *B. coriaceae, B. burgdorferi* B31, *B. burgdorferi* 297, *B. californiensis, B. afzalii, B. garinii, B. spielmanii* and *B. valensiana.*

Result Summary:

As shown in FIG. 1, in the columns numbered 1-3 under the heading "Relapsing Fever *Borrelia* species," antibodies to *B. hermsii*, TBRF *Borrelia* sp., and *B. coriaceae* were detected. In the columns numbered 1-7 under the heading "Lyme Disease *Borrelia* species," only antibodies to 41 kDa were detected with the rabbit anti-*B. burgdorferi* specific serum samples. The numbers refer to the antibodies denoted in the FIGURE key.

Conclusion:

Based on the data presented above, the TBRF ImmunoBlot is very specific for the detection of TBRF *Borrelia* specific antibodies.

Example 3

TBRF *Borrelia* ImmunoBlots Validation Study—Clinical Sensitivity and Specificity A total of 171 patient samples were tested as per TBRF *Borrelia* ImmunoBlot IgM and IgG protocols to determine clinical sensitivity and specificity. The following patient samples (Table 1) were tested as per TBRF *Borrelia* Immunoblot IgM and IgG test protocols. The ImmunoBlots were read by in-house criteria. The ImmunoBlot (IgM or IgG) was considered positive if 2 of the following bands were present: 21-23, 41, 70-75 kDa and GlpQ. If only one of the following bands is present, the ImmunoBlot was considered boarder-line positive: 21-23, 70-75 kDa and GlpQ. Results are summarized below in Tables 2a, 2b and 2c.

TABLE 1

List of Patient Samples Tested

| Study Set # | Source | Samples | n |
|---|---|---|---|
| Set 1 | In-house | 34 samples tested by TBRF Western blots (Lyme-like symptoms, most negative by Lyme Western Blot and Lyme ImmunoBlots) | 34 |
| Set 2 | In-house | 10 samples - 2 samples/patient collected at different time points (Negative by Lyme Western and ImmunoBlots) | 20 |
| Set 3 | CDC | CDC - Specificity Samples (Provided Blinded by CDC) | 50 |
| Set 4 | NY biologics | Specificity Samples (purchased from NY Biologies) | 25 |
| Set 5 | In-house | Autoimmune and Allergy patient samples (Previously left over PT samples) | 42 |
| | | Total Samples | 171 |

TABLE 2a

Results: Overall Summary.
Table 2: Clinical Sensitivity - Overall Summary (see Table 2a and 2b)

| | | | Lyme ImmunoBlot | | | TBRF ImmunoBlot | | |
|---|---|---|---|---|---|---|---|---|
| Sample | Size | Result | IgM | IgG | IgM &/ or IgG | IgM | IgG | IgM &/ or IgG |
| Set 1 | 34 | Positive | 2 | 1 | 2 | 15 | 8 | 18 |
| | | Negative | 32 | 33 | 32 | 19 | 26 | 16 |
| Set 2 | 10 | Positive | 0 | 0 | 0 | 6 | 3 | 7 |
| | (old) | Negative | 10 | 10 | 10 | 4 | 7 | 3 |
| | 10 | Positive | 0 | 0 | 0 | 8 | 5 | 10 |
| | (new) | Negative | 10 | 10 | 10 | 2 | 5 | 0 |
| Total | 54 | Positive | 2 | 1 | 2 | 29 | 16 | 35 |
| | | Negative | 52 | 53 | 52 | 25 | 38 | 19 |

TABLE 2b

Performance of TBRF Immunoblot on Clinical Samples
Set 1: Patients with Lyme-like symptoms

| Patients Samples with antibodies to: | n | IgM (+) | IgG (+) | IgM and/or IgG (+) |
|---|---|---|---|---|
| Patients negative for Lyme | 30 | 15 | 9 | 18 |
| *Bartonella* | 2 | 0 | 0 | 0 |
| *Ehrlichia* | 2 | 0 | 0 | 0 |
| Total Positive | | 15 | 9 | 18 |
| Total Negative | | | | 16 |

To see how a patient's response immunologically to infection two samples were collected from each of 10 patients (including patients with a history of a tick bite and TBRF PCR positives). Results are presented below in Table 2c.

TABLE 2c

Performance of TBRF Immunoblot on 10 Positive Clinical Samples
Set 2: Patients with Lyme-like Symptoms, negative by Lyme ImmunoBlots and Lyme Western blots (10 patient samples collected at 2 time points)

| Patient Samples | n | IgM (+) | IgG (+) | IgM and/or IgG (+) |
|---|---|---|---|---|
| 1st collection | 10 | 6 | 3 | 7 |
| | | 4 | 7 | 3 |
| 2nd collection | 10 | 8 | 5 | 10 |
| (6 weeks to 2 years latter) | | 2 | 5 | 0 |

Sensitivity:

Based on the data presented above for patients with Lyme-like symptoms, of the 44 patients (total 54 samples) with Lyme-like symptoms, 2 patients had antibodies to *B. burgdorferi* and TBRF *Borrelia;* 29 patients had antibodies to TBRF *Borrelia*. Four patients with other tick-borne diseases were negative by TBRF ImmunoBlot. Two sets of serum samples were collected from 10 patients, to see patient's immune response to infection. We collected two samples at different time points from 10 patients (including patients with a history of a tick bite and/or TBRF PCR positive samples). The second sample was collected 6 weeks to 2 years after the first sample (See Table 2b and Table 2c for detailed results). As shown above, 7 patients (4 IgM (+), 1 IgG (+) and 2 with IgM and IgG) were positive initially. When the second sample was tested all patients were positive, 5 IgM (+), 2 IgG (+) and 3 IgM and IgG (+).

Specificity:

Based on the data presented below in Table 3, the specificity of the TBRF *Borrelia* ImmunoBlot was 95.0% for IgM and 97.5% for IgG.

Conclusion:

The specificity of TBRF ImmunoBlot was 95.0% for IgM and 97.5% for IgG. With 10 patients (Set 2), we demonstrated that the immune response varied between individuals.

The results show that the TBRF ImmunoBlots can be used in to detect TBRF *Borrelia*-specific antibodies in patients suspected of TBRF Borreliosis. The results can be used by the physician in conjunction with patient history and symptoms. Detailed results are summarized below in Table 3.

TABLE 3

Clinical Specificity - Overall Summary

| Source | Sample Types | n | IgM (+) | IgG (+) | IgM and/or IgG (+) |
|---|---|---|---|---|---|
| 50 CDC Samples (n = 50, Set 3) | Endemic Controls | 10 | 0 | 0 | 0 |
| | Fibromyalgia | 5 | 0 | 0 | 0 |
| | Mononucleosis | 5 | 0 | 0 | 0 |
| | Multiple Sclerosis | 5 | 1 | 0 | 1 |
| | Non-endemic Controls | 10 | 0 | 0 | 0 |
| | Periodontitis | 5 | 0 | 0 | 0 |
| | Rheumatoid Arthritis | 5 | 1 | 0 | 1 |
| | Syphilis | 5 | 0 | 1 | 1 |
| | Antibodies to: | n | IgM (+) | IgG (+) | IgM and/or IgG (+) |
| New York Biologies (n = 25, Set 4) | Rapid Plasma Reagin (RPR) | 8 | 1 | 1 | 2 |
| | Epstein-Barr virus (EBV) | 4 | 0 | 0 | 0 |
| | Human immunodeficiency virus 1 (HIV-1) | 4 | 0 | 0 | 0 |
| | Cytomegalovirus (CMV) | 5 | 0 | 1 | 1 |
| Autoimmune and Allergy (n = 42, Set 5) | Antinuclear antibody (ANA+) | 5 | 0 | 0 | 0 |
| | Antinuclear antibody (ANA−) | 4 | 0 | 0 | 0 |
| | DNA (+) | 1 | 0 | 0 | 0 |
| | Rheumatoid factor (+) | 9 | 2 | 0 | 2 |
| | Rheumatoid Factor (−) | 8 | 0 | 0 | 0 |
| | IgG (+) | 13 | 1 | 0 | 1 |
| | Spec. IgE (+) | 4 | 0 | 0 | 0 |
| | Spec. IgE (−) | 2 | 0 | 0 | 0 |
| In-house (n = 4, Set 1) | *Bartonella henselae* | 2 | 0 | 0 | 0 |
| | Human Granuloytic *Ehrlichia* | 2 | 0 | 0 | 0 |
| False Positive | | | 6 | 3 | 9 |
| True Negative | | 121 | 115 | 118 | 112 |
| Specificity | | | 95% | 97.5% | 93% |

We claim:

1. A composition comprising one or more amino acid sequences bound to a solid support, wherein the one or more bound amino acid sequences consist of amino acid sequences selected from the group consisting of SEQ ID NO: 9, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

2. The composition of claim 1, wherein said amino acid sequences are bound to a solid support selected from the group consisting of nitrocellulose, nylon, polyvinylidene difluoride (PVDF), magnetic beads, metal, plastic, and agarose.

3. A method of detecting antibodies to one or more of *B. hermsii, B. turicatae, B. miyamotoi, B. turcica*, and *B. coriaceae* amino acid sequences in a sample from a subject suspected of having tick-borne relapsing fever (TBRF), said method comprising:

providing a biological sample obtained from a subject suspected of having TBRF;

mixing the biological sample with one or more of the bound amino acid sequences of claim 1; and detecting a positive immunobinding reaction which indicates the presence of TBRF specific antibodies in the sample.

4. The method of claim 3, wherein biological sample is considered positive for TBRF if at least two bound amino acid sequences are detected.

5. The method of claim 3, wherein the bound amino acid sequences, complexed with antibodies to one or more of *B. hermsii, B. turicatae, B. miyamotoi, B. turcica*, and *B. coriaceae*, are detected using anti-human IgG or anti-human IgM antibody linked to a detectable moiety.

6. The method of claim 5, wherein said detectable moiety is selected from the group consisting of chromophores, radioactive moieties and enzymes.

7. The method of claim 5, wherein said detectable moiety comprises alkaline phosphatase.

8. The method of claim 5, wherein said detectable moiety comprises biotin.

9. The method of claim 4, wherein the at least two bound amino acid sequences detected are group-specific and are detected from the groups selected from: (1) 21-23 kDa; (2) 41 kDa; (3) 70-75 kDa; and (4) GlpQ; and wherein the at least two bound sequences are not specific for the same group.

* * * * *